(12) United States Patent
Magno et al.

(10) Patent No.: US 12,396,747 B2
(45) Date of Patent: Aug. 26, 2025

(54) ARTICULATING DEBRIDER BLADE TIP AND HANDPIECE CONTROL

(71) Applicant: GYRUS ACMI, INC., Westborough, MA (US)

(72) Inventors: Joey Magno, Dudley, MA (US); Michael Sansoucy, Wrentham, MA (US); Richard M. Braga, North Easton, MA (US); Scott Wudyka, Marlborough, MA (US)

(73) Assignee: Gyrus ACMI, Inc., Westborough, MA (US)

(*) Notice: Subject to any disclaimer, the term of this patent is extended or adjusted under 35 U.S.C. 154(b) by 377 days.

(21) Appl. No.: 17/814,979

(22) Filed: Jul. 26, 2022

(65) Prior Publication Data

US 2023/0030109 A1 Feb. 2, 2023

Related U.S. Application Data

(60) Provisional application No. 63/203,735, filed on Jul. 29, 2021, provisional application No. 63/203,733, filed on Jul. 29, 2021.

(51) Int. Cl.
 *A61B 17/32* (2006.01)
(52) U.S. Cl.
 CPC .............................. *A61B 17/32002* (2013.01)
(58) Field of Classification Search
 CPC .......... A61B 17/0469; A61B 17/00234; A61B 17/0487; A61B 17/068; A61B 17/2909; A61B 17/320016; A61B 17/32002; A61B 2017/2908; A61B 2017/2929; A61B 2017/0647; A61B 2017/00309; A61B 2017/0488
 See application file for complete search history.

(56) References Cited

U.S. PATENT DOCUMENTS

| 5,620,447 | A | * | 4/1997 | Smith | A61B 17/32002 606/180 |
| 5,851,212 | A | * | 12/1998 | Zirps | A61B 34/71 606/174 |
| 6,645,218 | B1 | * | 11/2003 | Cassidy | A61B 17/32002 606/170 |
| 2004/0225305 | A1 | * | 11/2004 | Ewers | A61B 17/0401 606/153 |

(Continued)

*Primary Examiner* — Tuan V Nguyen
(74) *Attorney, Agent, or Firm* — Schwegman Lundberg & Woessner, P.A.

(57) ABSTRACT

A handheld surgical instrument having a handpiece and a shaft extending from the handpiece is provided. The instrument includes a cutting implement disposed at a distal end of the shaft and an articulation portion disposed proximate to the cutting implement. The articulation portion includes a set of first slits and a set of second slits opposite the first set of slits. The articulation portion also has first and second passageways disposed in the slits along with first and second flat pull wires disposed in the passageways. The instrument also has an articulation control assembly that includes an articulator having first and second anchor points coupled with the first and second flat pull wires. The articulator moves the first flat pull wire in a first direction and moves the second flat pull wire in a second direction opposite the first direction during actuation.

11 Claims, 29 Drawing Sheets

(56) References Cited

U.S. PATENT DOCUMENTS

| | | | |
|---|---|---|---|
| 2010/0076260 A1* | 3/2010 | Taylor ................ | A61B 17/2909 600/118 |
| 2013/0066318 A1* | 3/2013 | Kerr .................... | A61B 18/085 606/171 |
| 2015/0320437 A1* | 11/2015 | Worrell .......... | A61B 17/320068 606/169 |

* cited by examiner

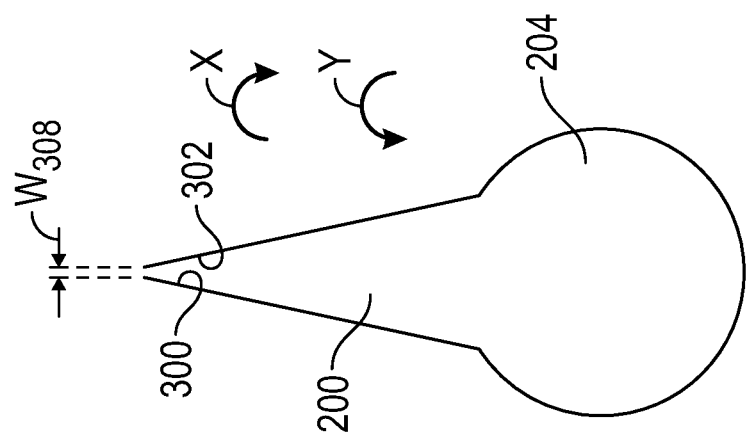
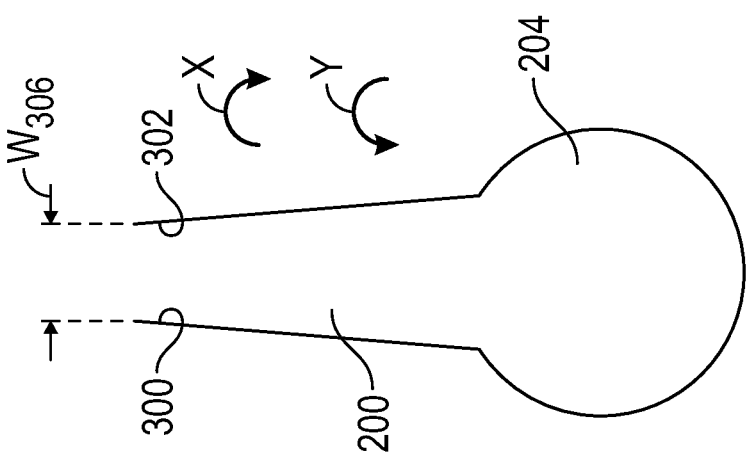
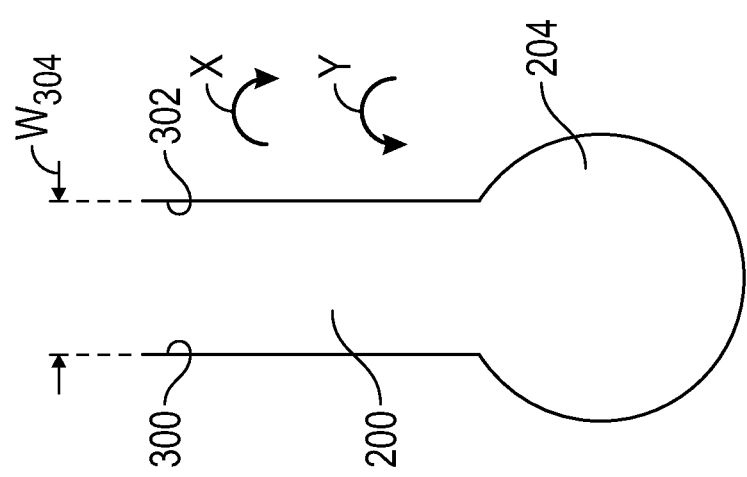

ARTICULATING DEBRIDER BLADE TIP AND HANDPIECE CONTROL

CROSS-REFERENCE TO RELATED APPLICATIONS

This application claims the benefit of priority to U.S. Provisional Patent Application Ser. No. 63/203,733, filed Jul. 29, 2021 and U.S. Provisional Patent Application Ser. No. 63/203,735 filed Jul. 29, 2021, the contents of which are hereby incorporated by reference in their entireties.

TECHNICAL FIELD

This document pertains generally, but not by way of limitation, to surgical devices that can be used for various surgical procedures. More specifically, but not by way of limitation, the present application relates to a handheld surgical instrument.

BACKGROUND

Occlusions within cavities of patients, such as sinus cavities, can cause a number of issues with a patient. These issues can include, for example, chronic rhinosinusitis, a deviated septum, nasal polyps, or the like. In order to remove these or other types of occlusions within cavities, a physician can use a handheld surgical instrument having a microdebrider or a drill. Microdebriders can be used with a variety of implements depending on the procedure being performed. A microdebrider can include a cutting implement that can oscillate, i.e., moves in a back and forth rotational motion or moves in a back and forth linear motion, and that can be used in Rhinologic procedures to remove softer tissues of the sinuses. For example, a pre-bent implement having cutting implements can be used when surgery is being performed at difficult to reach surgical sites, such as the aforementioned sinus cavities. In addition, straight implements can also be used to perform surgical procedures within sinus cavities. Moreover, cutting implements that can facilitate 360-degree rotation can also be used with a single microdebrider. Thus, a single microdebrider can be used for a variety of procedures with a variety of implements. As noted above, a drill can also be used. For example, a drill can be used in Otologic procedures to remove bone in, and around, the ear.

However, in situations where an implement is pre-bent, an angle at which the implement is pre-bent can limit how a microdebrider having the pre-bent implement can be used. For example, the implement can be pre-bent at an angle that does not allow the usage of the microdebrider within certain areas of a sinus cavity. Similarly, in situations where straight implements are used, the same problems may arise. In particular, the straight implement may not allow the usage of the microdebrider within certain areas of a sinus cavity.

Accordingly, what is needed is a handheld surgical device, such as a microdebrider or a drill, having an implement that can be bent by a user over a range of angles depending on the access requirements of a surgical site.

SUMMARY

Examples of the present disclosure relate to a handheld surgical instrument that facilitates articulation of a distal portion of the handheld surgical instrument while the distal portion is positioned at a surgical site. Articulation of the distal portion can be controlled at a handpiece of the handheld surgical instrument. The handheld surgical instrument can include a pull wire, such as a flat pull wire, that is anchored at the distal portion of the handheld surgical instrument and can extend towards the handpiece. The handpiece can include an assembly that can push and/or pull the flat pull wire. In an embodiment, the assembly can be controlled to push and/or pull the flat wire such that articulation of the distal portion can be controlled.

BRIEF DESCRIPTION OF FIGURES

FIGS. 3A-3C show an articulation of a slit of the articulation portion shown with reference to FIG. 2.

DETAILED DESCRIPTION

Examples of the present disclosure relate to a handheld surgical instrument that facilitates articulation of a distal portion of the handheld surgical instrument while the distal portion is positioned at a surgical site. Articulation of the distal portion can be controlled at a handpiece of the handheld surgical instrument. In an embodiment, the handheld surgical instrument can include an outer blade which can remain stationary during a surgical procedure and an inner blade disposed within the outer blade that can rotate within the outer blade during operation of the handheld surgical instrument. A distal portion of the outer blade can include opposing slits, which facilitates articulation in a first direction such that a tip of the handheld surgical instrument can have a bend radius up to two inches while articulating up to ninety degrees. The slits can be configured such that the distal portion only articulates in the first direction.

In an embodiment, articulation of the distal portion can be controlled at the handpiece of the handheld surgical instrument. The handheld surgical instrument can include a pull wire, such as a flat pull wire, that is anchored at the distal portion of the handheld surgical instrument and can extend towards the handpiece. The handpiece can include an assembly that can push and/or pull the pull wire. In an embodiment, when the assembly is actuated to pull the pull wire, the distal portion can articulate in order to bend the distal portion of the handheld surgical instrument. Moreover, in an embodiment, the assembly can be actuated to push the pull wire, thereby straightening the distal portion of the handheld surgical instrument.

Figure 1:
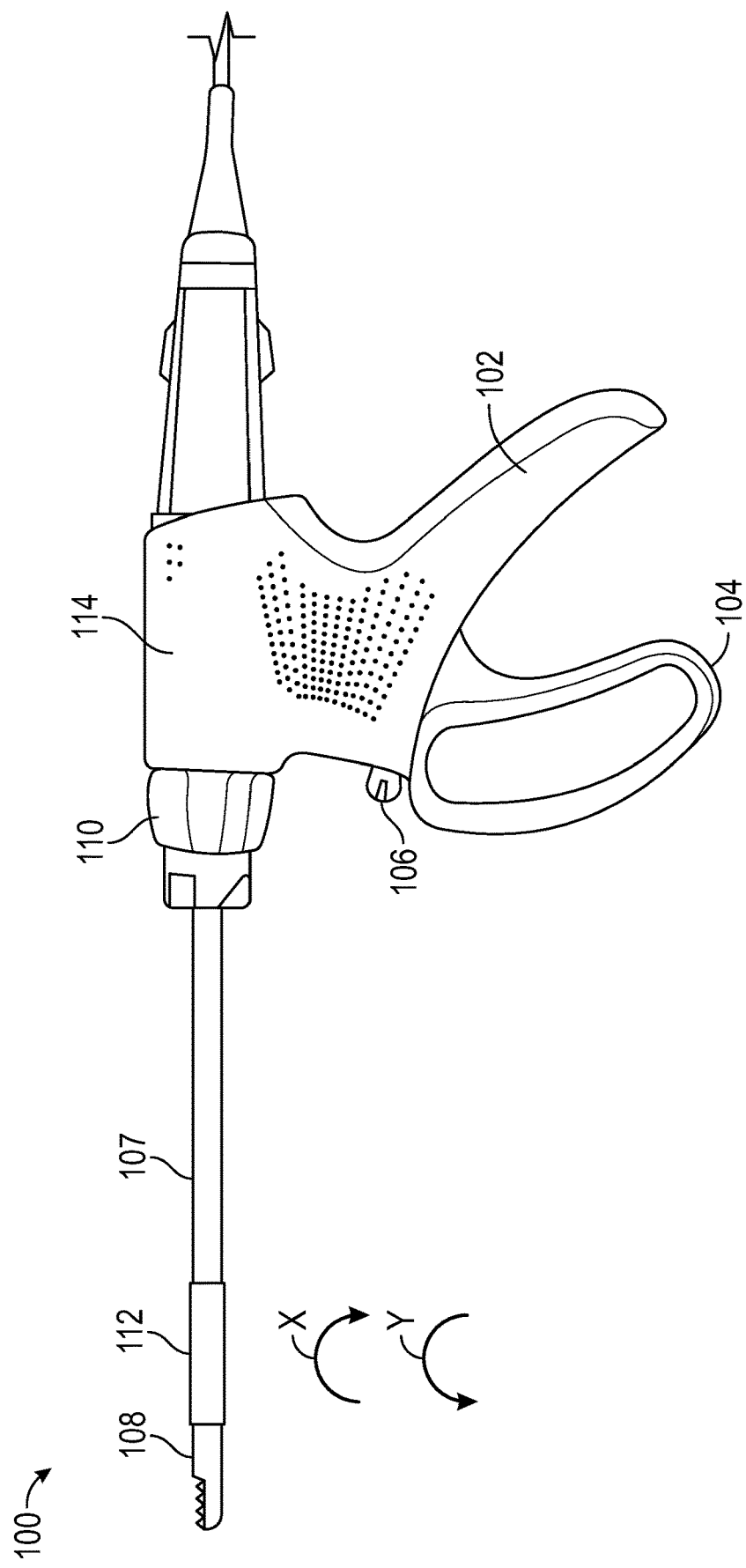
FIG. 1 illustrates a handheld surgical instrument.

Now making reference to the Figures, and more specifically FIG. 1, a handheld surgical instrument 100 is shown. The handheld surgical instrument 100 can include a handpiece 102, a handle gear 104, and an actuating mechanism 106. The handheld surgical instrument 100 can also include a shaft 107 that extends from a proximal end of the handheld surgical instrument 100 to a distal end of the handheld surgical instrument 100 where a cutting implement 108 is disposed at a distal end of the shaft 107. In an example, the handheld surgical instrument 100 can be a microdebrider that can be used to treat various rhinological conditions, such as chronic rhinosinusitis, a deviated septum, nasal polyps, or the like. While not shown, the handheld surgical instrument 100 can include a rotating blade disposed within the cutting implement 108 that extends from the cutting implement 108 to the proximal end of the handheld surgical instrument. the rotating blade can work in conjunction with the cutting implement 108 to resect tissue during use of the handheld surgical instrument 100. Therefore, the cutting implement 108 can function as an outer blade and the rotating blade can function as an inner blade that rotates within the cutting implement 108.

The cutting implement 108 can be any type of blade that can be used for various procedures, such as functional endoscopic sinus surgery (FESS) procedures. The type of blades that can be used for the cutting implement 108 can include a standard blade with or without suction capability, bipolar and/or monopolar energy blades that can be used for hemostasis during a surgical procedure, or a rotatable blade. Moreover, the cutting implement 108 can be a straight blade, an angled blade, or a turbinate blade. In addition, while the cutting implement 108 is shown, the handheld surgical instrument 100 can also include a burr in place of the cutting implement 108 for FESS procedures, such as a diamond bullet burr, a diamond ball burr, a diamond tapered burr, a fluted barrel burr, or an angled burr. In addition, the handheld surgical instrument 100 can be used for procedures other than FESS procedures. Moreover, in further examples, the handheld surgical instrument 100 can be used as a dental drill, as an ontology drill for ENT applications, or with a Dremel™. The cutting implement 108 can be rotated with a nose cone 110 and can include an articulation portion 112 along with a housing 114 adjacent the nose cone 110. It should be noted that in some embodiments, articulation may only occur in one plane.

The articulation portion 112 can be configured to allow articulation of the cutting implement. The articulation portion can be configured to allow a user to articulate the distal end of the handheld surgical instrument 100. For example, the user can be a surgeon and when the surgeon maneuvers the cutting implement 108 and the distal end of the handheld surgical instrument 100 to a surgical site, the surgeon can articulate the distal end of the handheld surgical instrument 100. By articulation of the distal end, the cutting implement 108 can be properly positioned at the surgical site and the surgeon can resect tissue.

Figure 2:
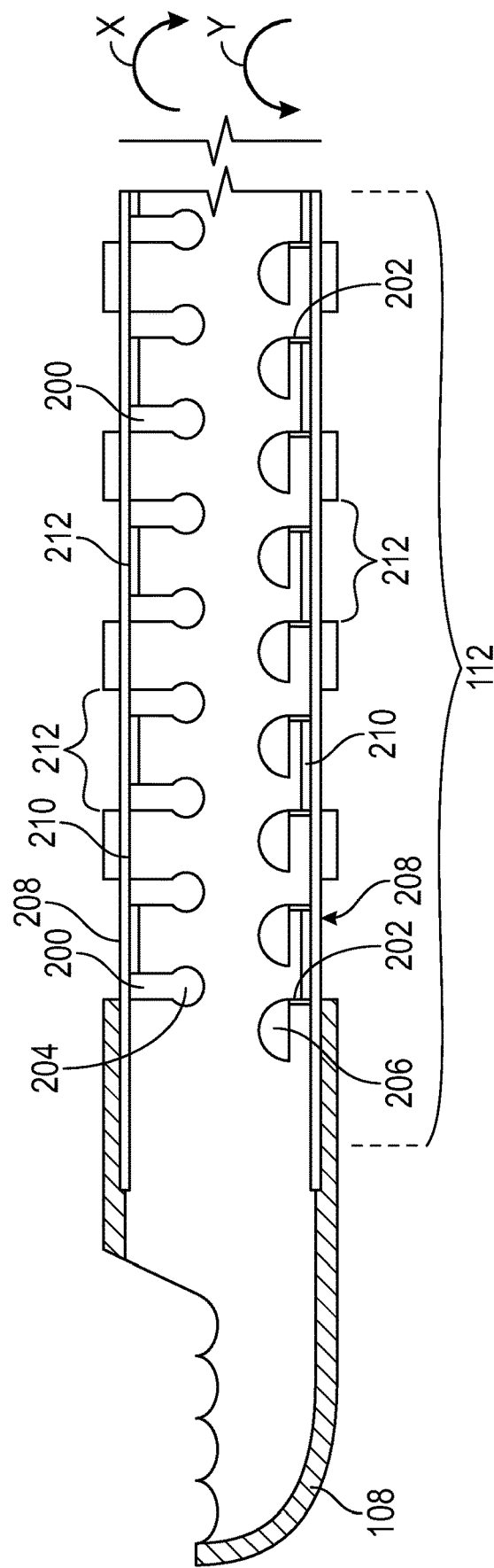
FIG. 2 illustrates an articulation portion of the handheld surgical instrument shown with reference to FIG. 1.

In order to allow articulation of the cutting implement 108, the articulation portion 112 can be formed of any material that allows for bending of the articulation portion 112. Examples of materials that can be used can include a soft metal, polyurethane, a plastic, or the like. Regardless of the material used to form the articulation portion 112, in an example, as shown with reference to FIG. 2, the articulation portion 112 can include slits 200 and 202 that can be disposed opposite to each other at the articulation portion 112. Moreover, as may be seen with regards to FIG. 2, the slits 200 can be offset from the slits 202. The slits 200 and 202 can be configured to allow articulation of the articulation portion 112 in a direction X and a direction Y. In particular, the slit 200 can include a flex region 204 which can allow for flexing of the slit 200 during articulation of the articulation portion 112. More specifically, the flex region 204 can allow side walls of the slit 200 to rotate about the directions X and Y, thereby allowing articulation of the slit 200 and the articulation portion 112.

Figure 4A:
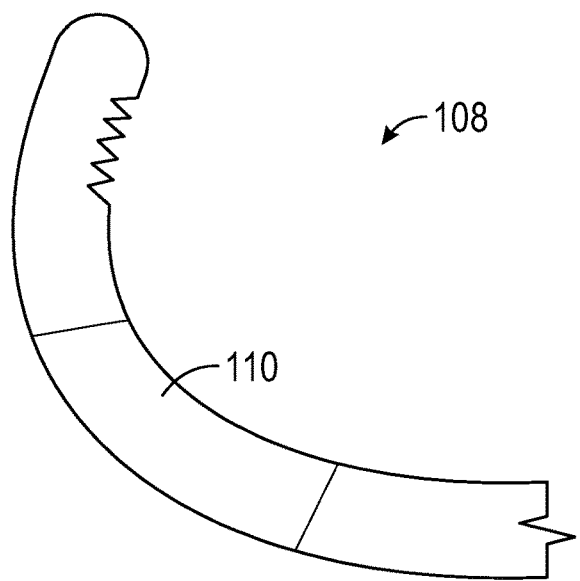
FIGS. 4A and 4B illustrate articulation of the articulation portion of FIG. 2.

To further illustrate, making reference to FIGS. 3A-3C, which show the articulation of the slit 200, the slit 200 can include side walls 300 and 302 which can be separated by a distance $W_{304}$ from each other. During articulation of the articulation portion 112, the side wall 300 can move along the direction X and the side wall 302 can move along the direction Y such that the side walls 300 and 302 can move closer to each other and can have a distance $W_{306}$ therebetween, as shown with reference to FIG. 3B. Here, the articulation portion 112 can be articulated such that the cutting implement 108 can have the configuration shown with respect to FIG. 4A.

Figure 4B:
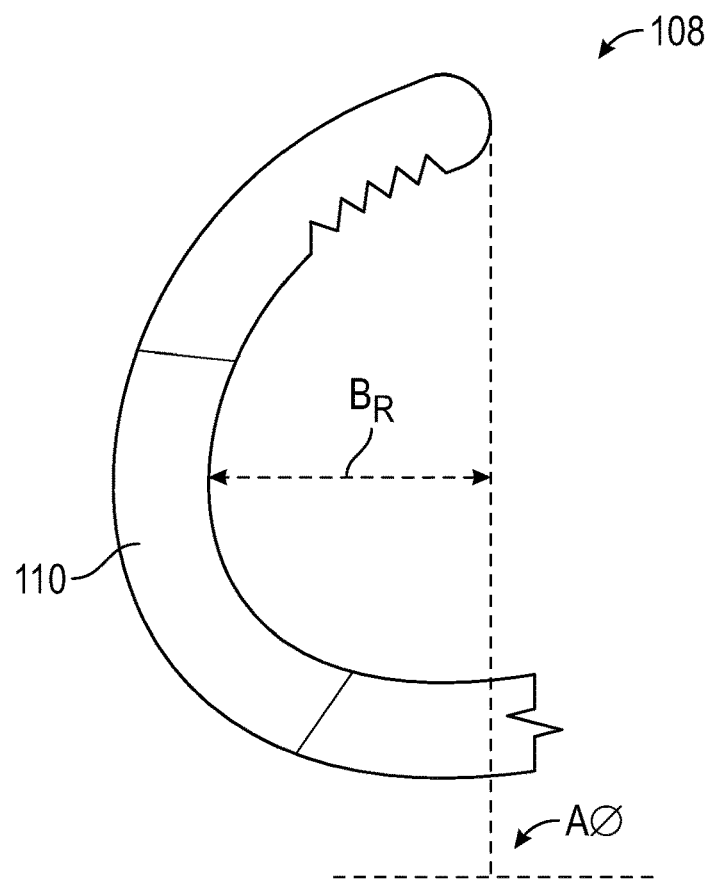

Additionally, should more articulation be required, the side wall 300 can move further along the direction X and the side wall 302 can move further along the direction Y such that the side wall 300 moves closer to the side wall 302 and can be separated by a distance $W_{308}$, as shown with reference to FIG. 3C. The articulation portion 112 can be articulated such that the cutting implement 108 can have the configuration shown with respect to FIG. 4B. As discussed herein, articulation of the cutting implement 108 from a substantially flat position to the position shown with reference to FIG. 4A can be described as positive articulation. Moreover, articulation of the cutting implement 108 from the position shown with reference to FIG. 4A to the position shown with reference to FIG. 4B can be also be described as positive articulation. Articulation of the cutting implement 108 from the position shown with reference to FIG. 4B to the position shown with reference to FIG. 4A can be described as negative articulation. In addition, articulation of the cutting implement 108 from the position shown with reference to either FIG. 4B or FIG. 4A to a substantially flat position can be described as negative articulation. As may be seen with reference to FIG. 4B, the articulation portion 112 can be configured such that the distal end of the cutting implement 108 can have a bend radius $B_R$ that is up to two inches. The bend radius $B_R$ can be in a range of about 0.75 to about 1.25 inches.

Returning attention to FIG. 2, the slit 202 can include a flex region 206 which can allow for flexing of the slit 202 during articulation of the articulation portion 112. More specifically, the flex region 206 can rotate about the directions X and Y, thereby allowing articulation of the slit 200 and the articulation portion 112. The flex region 206 can allow side walls of the slit 202 to rotate about the directions X and Y, thereby allowing articulation of the slit 202 and the articulation portion 112.

Figure 5C:
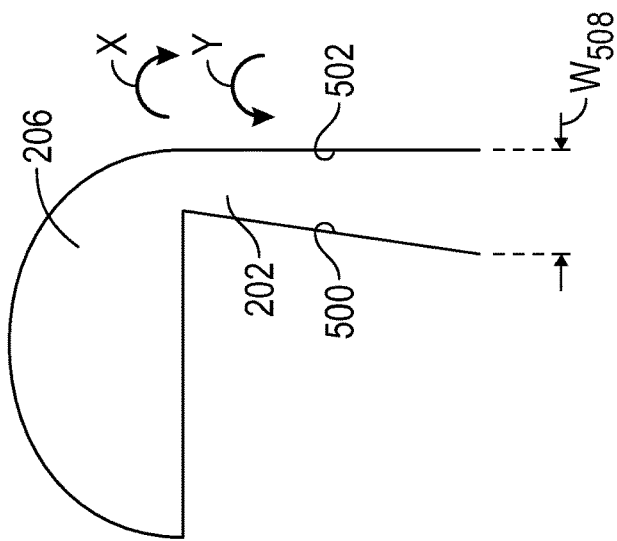
FIGS. 5A-5C illustrate the functioning of slits of the articulation portion of FIG. 2.
Figure 5B:
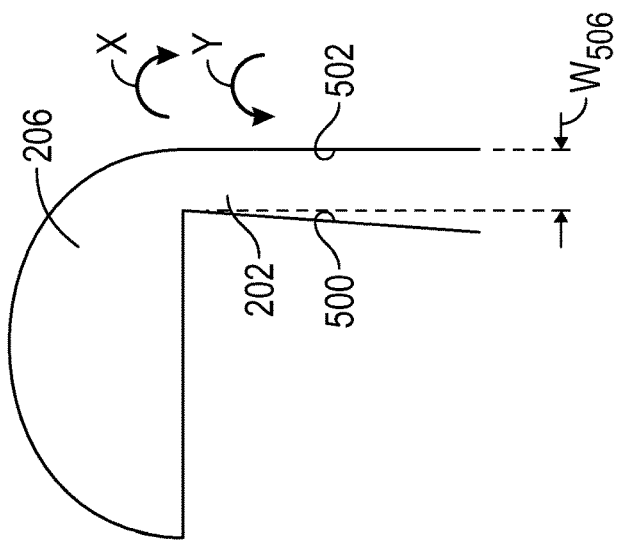
Figure 5A:
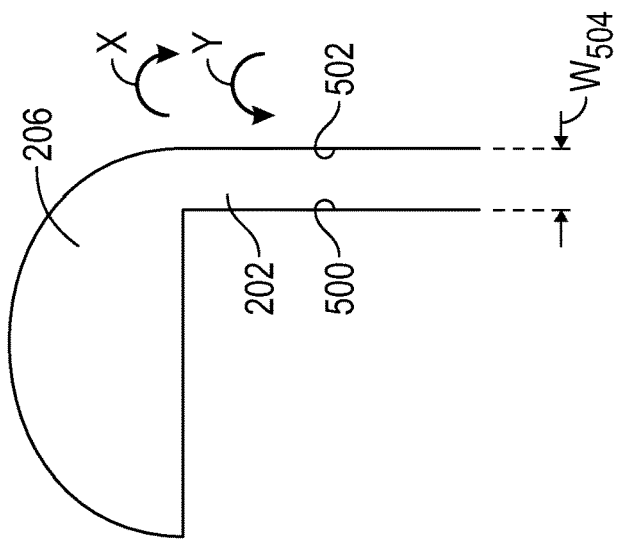

To further illustrate, making references to FIGS. 5A-5C, the slit 202 can include side walls 500 and 502 which can be separated a distance $W_{504}$ from each other. During articulation of the articulation portion 112, the side wall 500 can move along the direction X that the side walls 500 and 502 can move further apart and can have a distance $W_{506}$ therebetween, as shown with reference to FIG. 5B. The articulation portion 112 can be articulated such that the cutting implement 108 can have the configuration shown with respect to FIG. 4A.

Additionally, should more articulation, such as additional positive articulation, be required, the side wall 500 can move further along the direction X such that the side wall 500 moves further away from the side wall 502 and can be separated by a distance $W_{508}$, as shown with reference to FIG. 5C. The articulation portion 112 can be articulated such that the cutting implement 108 can have the configuration shown with respect to FIG. 4B. It should be noted that as the side wall 500 moves as discussed with reference to FIGS. 5A-5C, the side wall 500 can simultaneously move with the side walls 300 and 302, as discussed above with regards to FIGS. 3A-3C.

Figure 6:
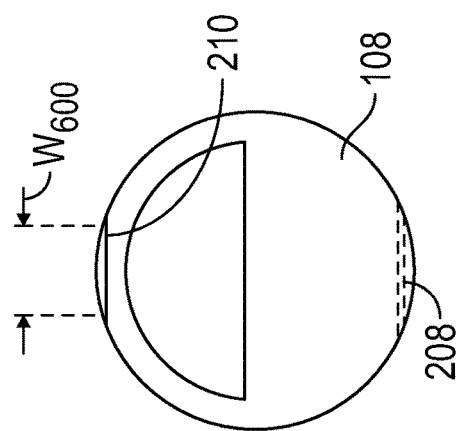
FIG. 6 illustrates a sectional view of a cutting portion of the handheld surgical instrument of FIG. 1.

Returning reference to FIG. 2, in order to control the articulation of the articulation portion 112, the handheld surgical instrument 100 can include flat pull wires 208 that can be disposed opposite each other on the cutting implement 108. The flat pull wires 208 can be formed of any material that allows for articulation of the flat pull wires 208. Examples of materials that can be used can include a soft metal, polyurethane, a plastic, or the like. As shown with reference to FIG. 2, the flat pull wires 208 can be disposed at the articulation portion 112 at the slits 200 and 212. The cutting implement 108 can include passageways 210 through which the flat pull wire 208 can pass in the cutting implement 108, as shown with reference to FIGS. 2 and 6. Furthermore, the articulation portion 112 can include areas 212 within which the flat pull wires 208 are exposed. Articulation of the articulation portion 112 can occur at the cutting implement areas 212.

Figure 7:
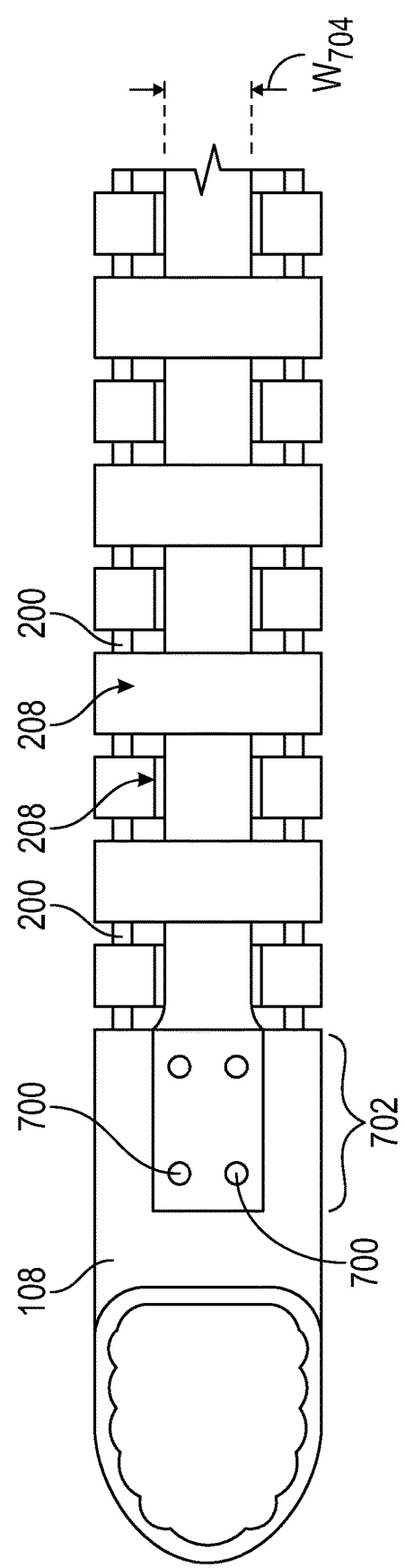
FIG. 7 is a top view of a cutting portion of the handheld surgical instrument of FIG. 1.

The flat pull wires 208 can anchor with the cutting implement 108 at anchor points 700 as shown with reference to FIG. 7. The flat pull wires 208 can anchor with the cutting implement 108 at the anchor points 700 at an anchoring area 702 with soldering, spot welding, threaded fasteners, rivets, or the like. Furthermore, the flat pull wires 208 can be anchored to the cutting implement 108 at the anchoring area with an adhesive, such as an epoxy, a glue, or the like. One of the flat pull wires 208 is anchored at the anchoring area 702 located adjacent to a cutting window of the cutting implement 108. In other words, the cutting window and one of the flat pull wires 208 are disposed on same side of the shaft 107. The flat pull wires 208 can have a width $W_{704}$ that can be in a range of about 0.06 inches to about 0.18 inches. However, the width $W_{704}$ can vary depending on a thickness of the flat pull wires 208 that can accommodate a given flexibility and tensile strength requirement. The cutting implement passageway can have a width $W_{600}$ that can be in a range of about 0.08 inches to about 0.20 inches. In addition to having a flat configuration as shown with reference to FIGS. 2 and 7, the flat pull wire 208 can have a circular configuration where a cross-section of the flat pull wire 208 is circular, an oval configuration where a cross-section of the flat pull wire 208 is in the shape of an oval, or any other type of configuration. Moreover, the cutting implement passageway 210 can have a configuration that complements the flat pull wire 208. Thus, if the pull wire 208 has a circular or oval configuration, the cutting implement passageway 210 can have a circular or oval configuration. Moreover, the flat pull wires 208 can be formed of any semi-rigid material. Examples of materials that can be used for the flat pull wires 208 can include a bendable metal, such as aluminum, stainless steel, galvanized steel, plastics, or the like.

As noted above, a user, such as a surgeon, can articulate the distal end of the handheld surgical instrument 100 via the articulation portion 112 such that the cutting implement 108 can be properly positioned at a surgical site. The user can articulate the distal end of the handheld instrument 100 along with the cutting implement 108 at the handpiece 102. The handpiece 102 can include an articulation control assembly 800 that can be used to articulate the distal portion of the handheld surgical instrument 100 and the cutting implement 108, as shown with reference to FIG. 8A. The articulation control assembly 800 can include the actuating mechanism 106 along with an actuating mechanism 802 in communication with the actuating mechanism 106 via a shaft 828.

The articulation control assembly 800 can include a housing 804 that can include portions 804A and 804B. The actuating mechanism 106 can be coupled to a spur gear 806 of the articulation control assembly 800 where the spur gear 806 can be disposed within the articulation control assembly housing portion 804A. The actuating mechanism 802 can be coupled to a spur gear 808 of the articulation control assembly 800. In an embodiment, the spur gear 808 can be disposed within the articulation control assembly housing portion 804B.

In an embodiment, the handle gear 104 can include a spline 810, which can operatively couple with the spur gear 806. The handle gear 104 can also include a spline 812, which can operatively couple with the spur gear 808. Moreover, the articulation control assembly 800 can include a one way bearing 814 disposed within a recess 816 of the spur gear 806 along with another one way bearing 818 disposed within a recess 820 of the spur gear 808.

Figure 9:
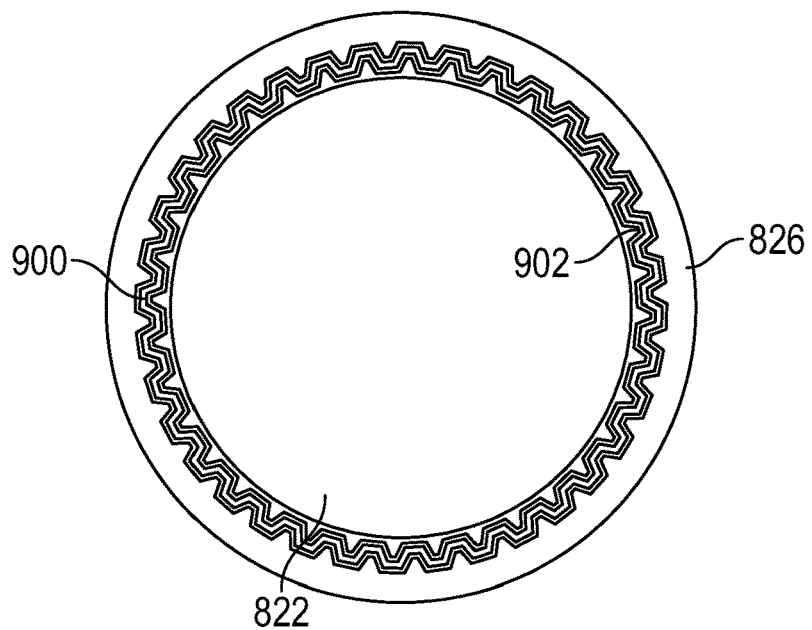
FIG. 9 illustrates the coupling of an articulator of the articulation control assembly of FIGS. 8A and 8B with a spline in accordance with at least one example of the present disclosure.
Figure 10:
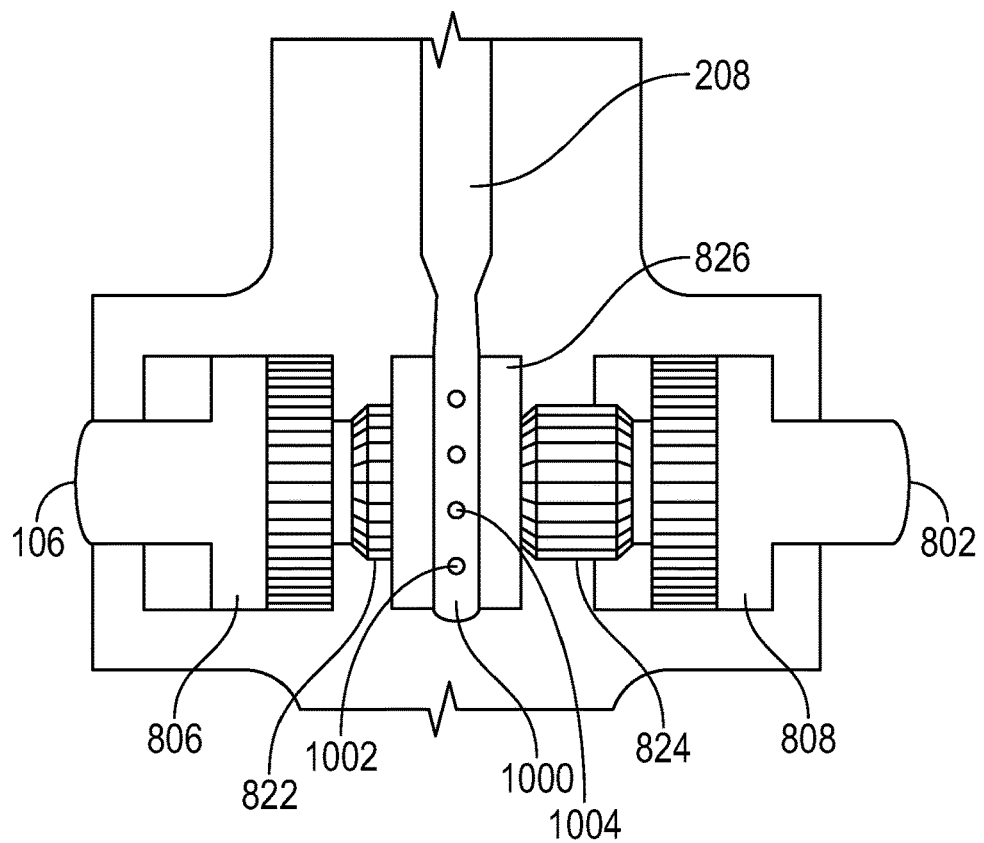
FIG. 10 is a top view of the articulation control assembly of FIGS. 8A and 8B in accordance with at least one example of the present disclosure.

In an embodiment, the articulation control assembly 800 can include splines 822 and 824, which, in an embodiment, can be configured to operatively couple with an articulator 826. In an embodiment, the articulator 826 can be a gear and can include gear teeth 900 that are complimentary to gear teeth 902 of the spline 822, a shown with reference to FIG. 9. In addition, the articulator 826 can also include recesses 827 within which an end 1000 (FIG. 10) of the flat pull wire 208 can be disposed. In an embodiment, the pull wire end 1000 anchors to the pull wire gear recess 827. In an embodiment, the pull wire end 1000 can be anchored within the pull wire gear recess 827 with soldering, spot welding, threaded fasteners, rivets, or the like. Furthermore, the pull wire end 1000 can be anchored within the pull wire gear recess 827 with an adhesive, such as an epoxy, a glue, or the like.

Figure 11A:
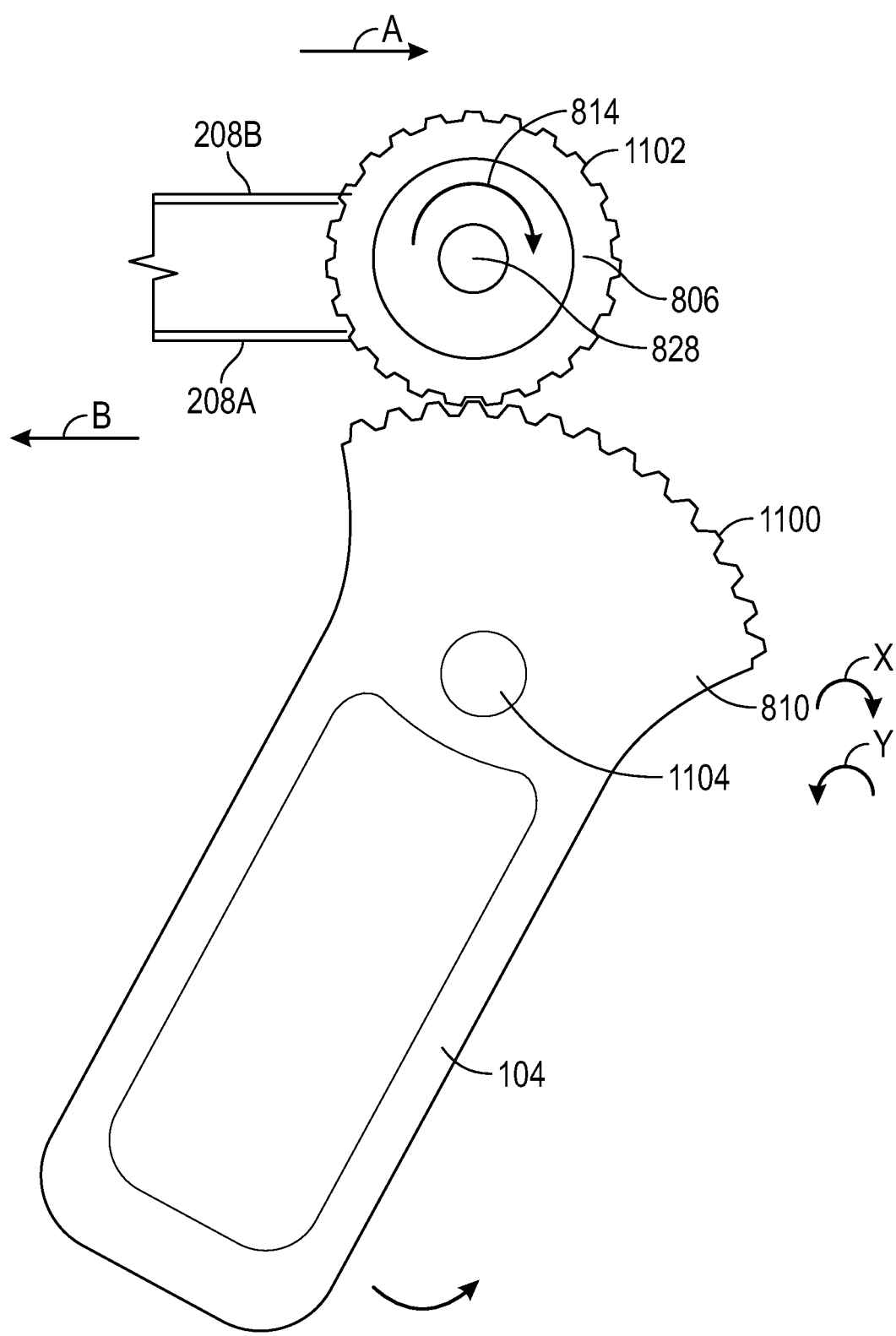
FIGS. 11A and 11B illustrate the use of a handle gear in conjunction with the articulation control assembly of FIGS. 8A and 8B to control articulation of a distal end of the handheld surgical instrument of FIG. 1 in accordance with at least one example of the present disclosure.

Returning attention to FIG. 8A, the articulation control assembly 800 can include the shaft 828 having ends 828A and 828B. The actuating mechanism 106 and the spur gear 806 can be disposed at the shaft end 828A while the actuating mechanism 802 and the spur gear 808 can be disposed at the shaft end 828B. When a user engages the actuating mechanism 106 such that the actuating mechanism moves along a direction A, the actuating mechanism 802 along with the spur gears 806 and 808 can move along the direction A. In addition, when a user engages the actuating mechanism 106 such that the actuating mechanism moves along the direction A, the splines 822 and 824 can also move along the direction A. In an embodiment, the spur gears 806 and 808 along with the splines 822 and 824 can continue to move along the direction A until an end 830 of the spur gear 808 nears a surface 832 of the articulation control assembly housing portion 804B. As may be seen with reference to FIG. 8A, when the spur gear end 830 abuts the articulation control assembly housing portion surface 832, the spur gear 806 engages with the handle gear teeth 1100 (FIG. 11A). In particular, the gear housing gear teeth 900 of 826 engage with the spline gear teeth 902 of 822.

In an embodiment, a user can use the handle gear 104 in conjunction with the articulation control assembly 800 to control articulation of the distal end of the handheld surgical instrument 100 via the articulation portion 112. In the embodiment shown with reference to FIG. 8A, the articulation control assembly 800 can be configured to articulate the distal end of the handheld surgical instrument 100 via the articulation portion 112 such that the cutting implement 108 moves along the direction X. To further illustrate, now making reference to FIG. 11A, a view of the handle gear 104 in cooperation with the spur gear 806 is shown in accordance with an embodiment. The handle gear 104 can include gear teeth 1100 which can engage with gear teeth 1102 of the spur gear 806 when a user rotates the handle gear 104 about a pivot 1104. In an embodiment, when a user pivots the handle gear 104 about the pivot 1104 along the direction Y, the handle gear teeth 1100 can engage with the spur gear teeth 1102, thereby causing the spur gear 806 to rotate along the direction X. When the spur gear 806 rotates along the direction X, the flat pull wire 208A can move along the direction B while the flat pull wire 208B can move along the direction A. More specifically, rotation of the spur gear 806 along the direction X can cause rotation of the articulator 826 along the direction X, thereby causing movement of the flat pull wire 208A along the direction B and movement of the flat pull wire 208B along the direction A. By virtue of the flat pull wire 208A moving along the direction B and the flat pull wire 208B moving along the direction A, the distal end of the handheld surgical instrument 100 articulates via the articulation portion 112 such that the cutting implement 108 moves along the direction X. For example, the distal end of the handheld surgical instrument 100 can articulate via the articulation portion 112 such that the cutting implement 108 can move from the substantially flat position shown with reference to FIG. 1 to an articulated position along the direction X, as shown with reference to FIGS. 4A and 4B and therefore have positive articulation. It should be noted that positive articulation is not limited to what is shown with reference to FIGS. 4A and 4B for purposes of this disclosure. In particular, the distal end of the handheld surgical instrument 100 can articulate via the articulation portion 112 such that there is more or less articulation than is shown with reference to FIGS. 4A and 4B during positive articulation.

In addition to articulating the distal end of the handheld surgical instrument 100 via the articulation portion 112 such that the cutting implement 108 moves along the direction X, the articulation control assembly 800 can be used for articulation along the direction Y. In particular, a user can move the actuating mechanism along a direction B such that an end 834 of the spur gear 806 contacts a surface 836 of the articulation control assembly housing, as shown with reference to FIG. 8B. Here, when the spur gear end 834 contacts the articulation control assembly housing surface 836, the spline 824 can engage with the handle gear spline 812, as shown with reference to FIG. 8B.

Figure 8A:
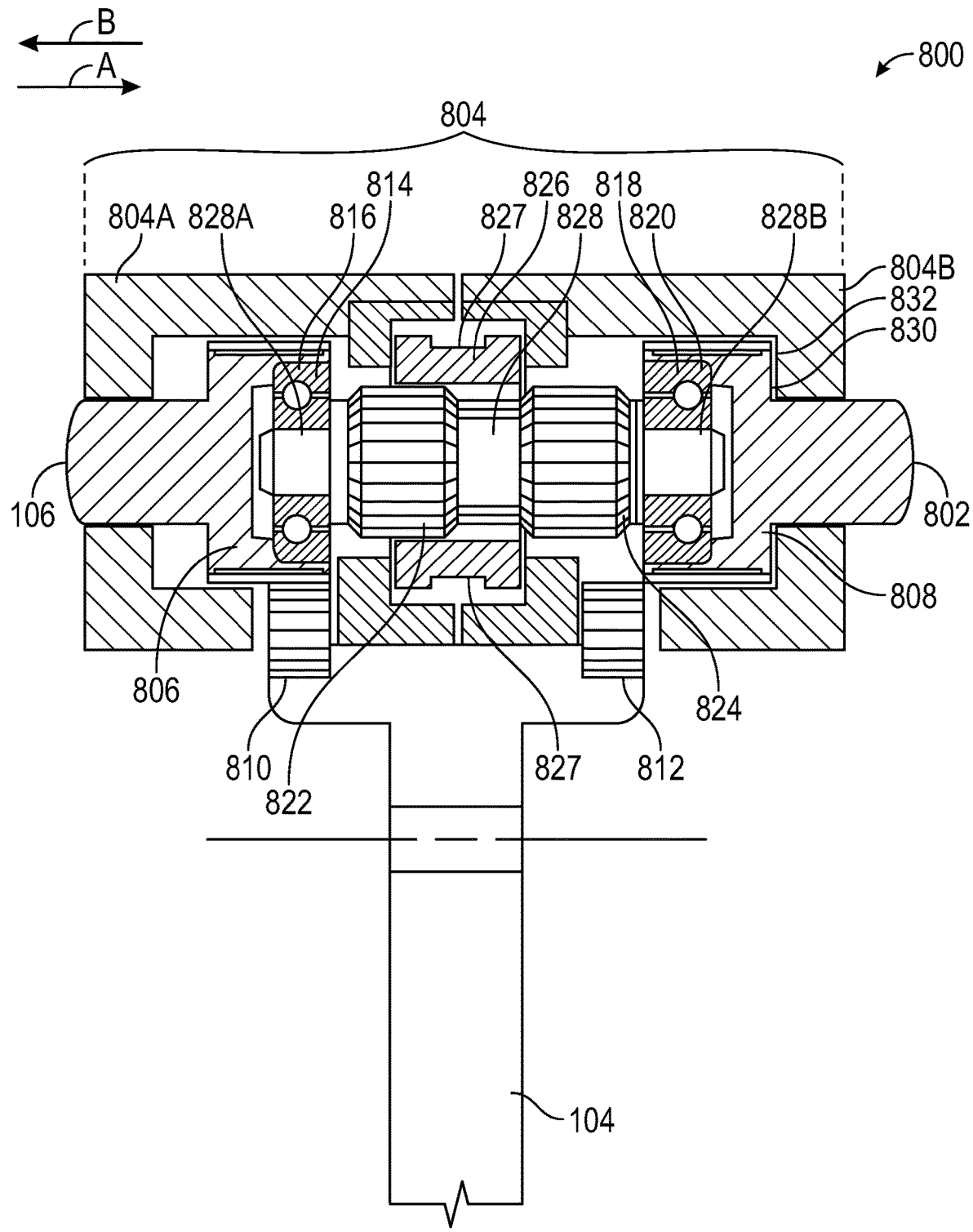
FIGS. 8A and 8B show an articulation control assembly of the handheld surgical instrument of FIG. 1 in accordance with at least one example of the present disclosure.
Figure 8B:
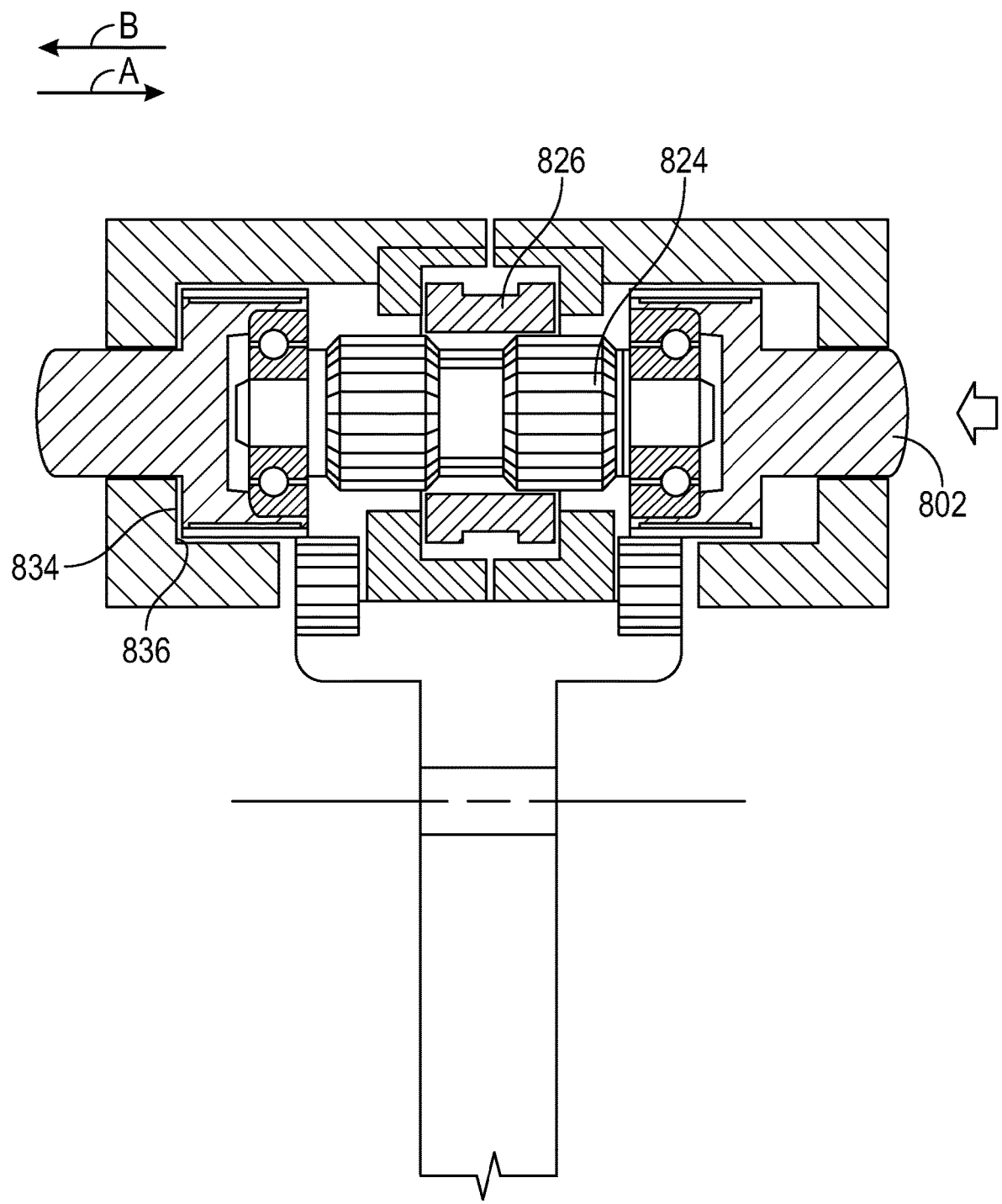
Figure 11B:
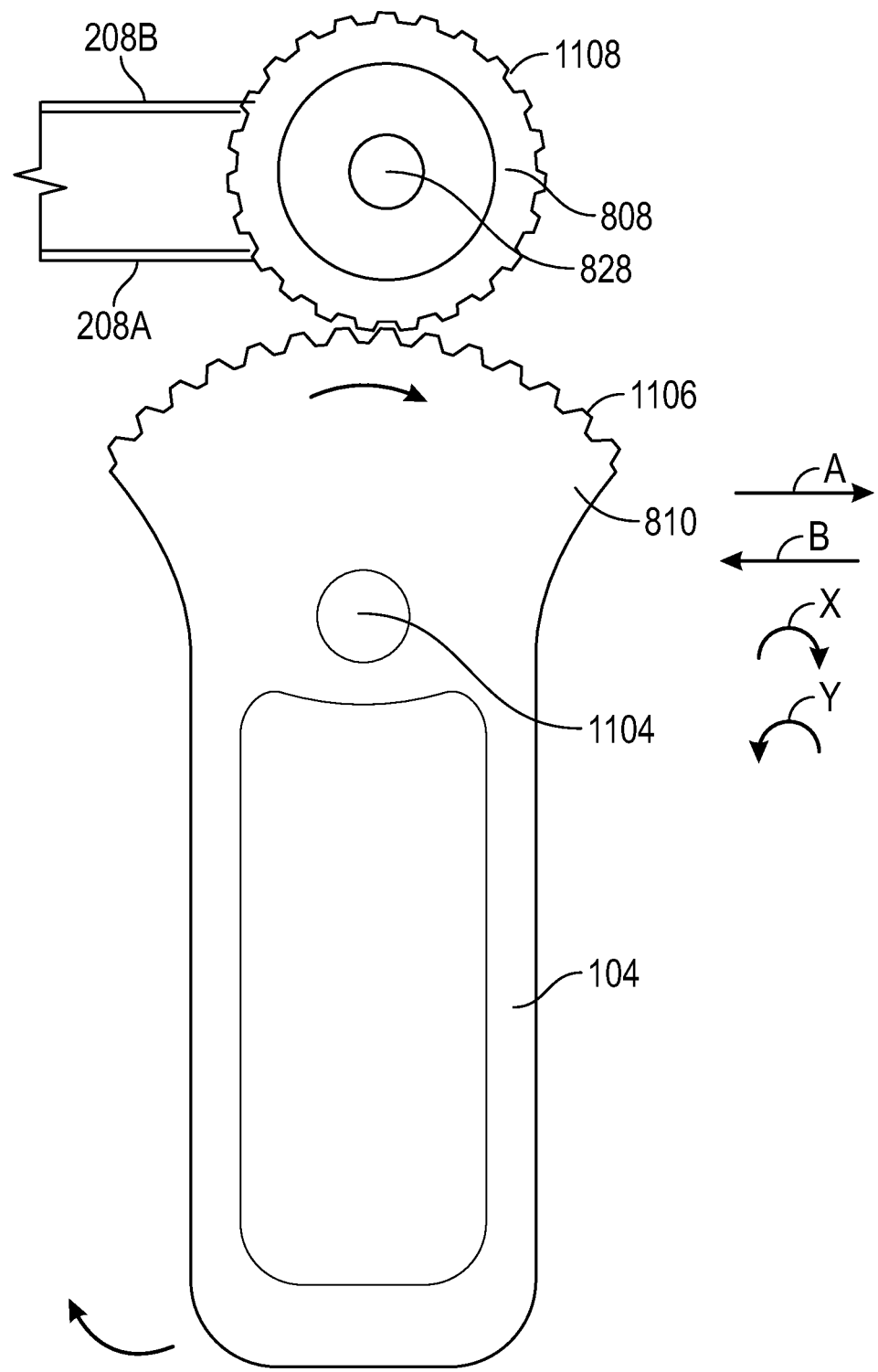

In the embodiment shown with reference to FIG. 8B, the articulation control assembly is configured to articulate the distal end of the handheld surgical instrument 100 via the articulation portion 112 such that the cutting implement 108 moves along the direction Y. To further illustrate, now making reference to FIG. 11B, a view of the handle gear 104 in cooperation with the spur gear 808 is shown in accordance with an embodiment. The handle gear 104 can include gear teeth 1106 which can engage with gear teeth 1108 of the spur gear 808 when a user rotates the handle gear 104 about a pivot 1104. In an embodiment, when a user pivots the handle gear 104 about the pivot 1104 along the direction X, the handle gear teeth 1106 can engage with the spur gear teeth 1108, thereby causing the spur gear 808 to rotate along the direction Y. When the spur gear 808 rotates along the direction Y, the flat pull wire 208A moves along the direction A while the flat pull wire 208B moves along the direction B. By virtue of the flat pull wire 208A moving along the direction A and the flat pull wire 208B moving along the direction B, the distal end of the handheld surgical instrument 100 articulates via the articulation portion 112 such that the cutting implement 108 moves along the direction Y. For example, the distal end of the handheld surgical instrument 100 can articulate via the articulation portion 112 such that the cutting implement 108 can move from the substantially curved position shown with reference to FIGS. 4A and 4B towards a position that is less curved than either of the positions shown with reference to FIGS. 4A and 4B, such as a negative articulation. Moreover, in accordance with the embodiments shown with regards to FIGS. 8B and 11B, the cutting implement 108 can be moved from the position shown with reference to FIG. 4A to the position shown with reference to FIG. 4B. It should be noted that articulation is not limited to what is shown with reference to FIGS. 4A and 4B. In particular, the distal end of the handheld surgical instrument 100 can articulate via the articulation portion 112 such that there is more or less articulation that is shown with reference to FIGS. 4A and 4B.

In addition to the articulation control assembly 800 shown with reference to FIGS. 8A and 8B, alternative articulation control assemblies can be used to articulate the distal end of the handheld surgical instrument 100 via the articulation portion 112 such that the cutting implement 108 moves along the directions X and Y. For example, the handheld surgical instrument 100 can include a ratchet articulation control assembly 1200 to articulate the distal end of the handheld surgical instrument 100 via the articulation portion 112, as shown with reference to FIG. 12.

Figure 12:
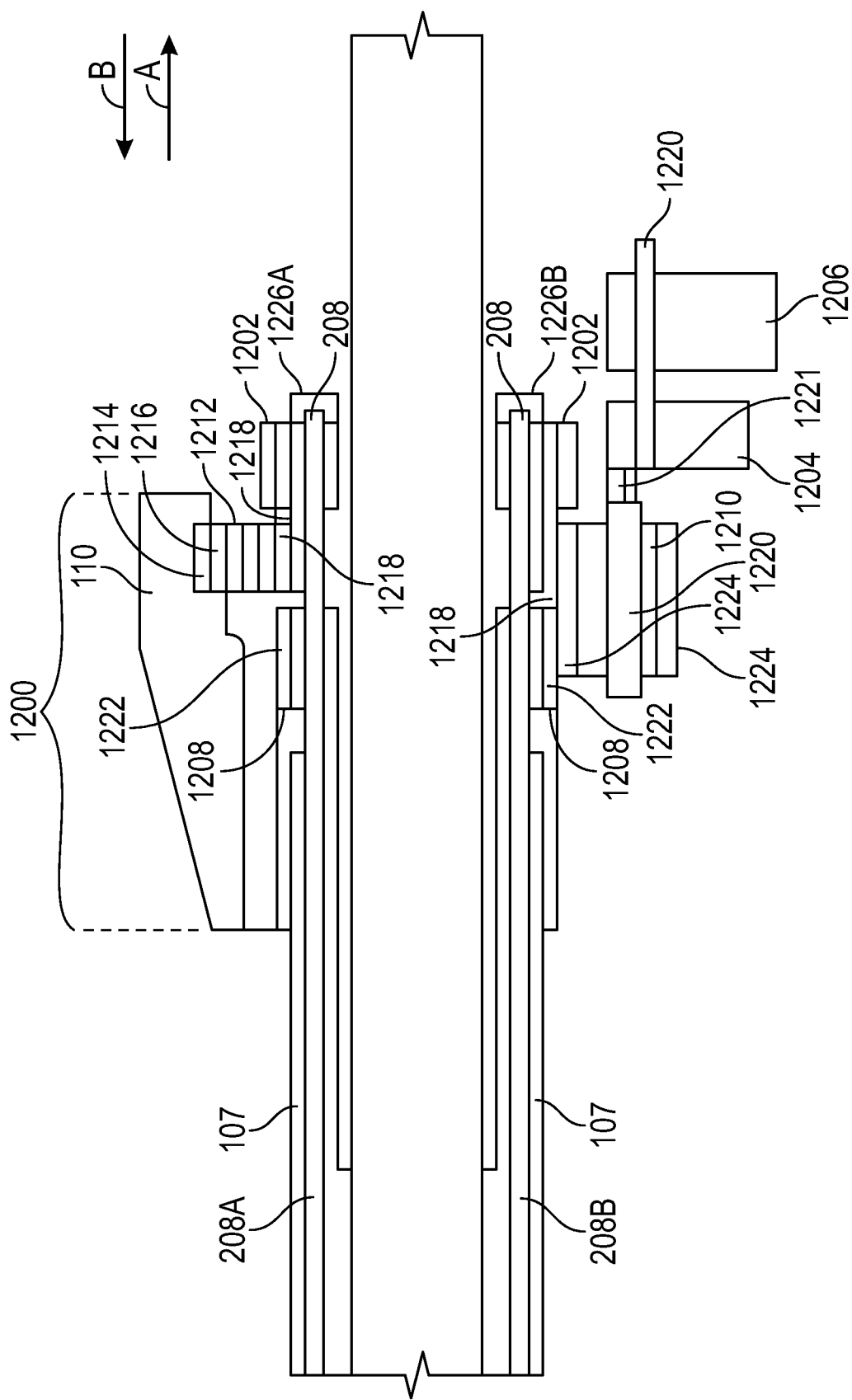
FIG. 12 shows an articulation control assembly of the handheld surgical instrument of FIG. 1 in accordance with at least one example of the present disclosure.

In an embodiment, the ratchet control assembly 1200 can include the nose cone 110 along with an articulator 1202, a cam 1204, and a switch lever 1206. It should be noted that only an upper half of the nose cone 110 is shown in FIG. 12. In addition, the ratchet control assembly 1200 can include an outer flex gear 1208, a handpiece idler gear 1210, and a nose cone idler gear 1212 where the nose cone idler gear 1212 can be coupled to the nose cone 110 such that rotation of the nose cone 110 can rotate the nose cone gear 1212. Specifically, the nose cone 110 can include gear teeth 1214 and the nose cone idler gear 1212 can include gear teeth 1216 that complement and mesh with the nose cone gear teeth 1214. In an embodiment, the articulator 1202 can be a ratchet gear. Furthermore, the nose cone idler gear 1212 can couple with the articulator 1202 via the nose cone idler gear teeth 1216 and ratchet gear 1218 of the articulator 1202. In an embodiment, the cam 1204, the switch lever 1206, and the handpiece idler gear 1210 can be operatively coupled with each other via ratchet control assembly shafts 1220 and 1221, as shown with reference to FIG. 12.

Figure 16A:
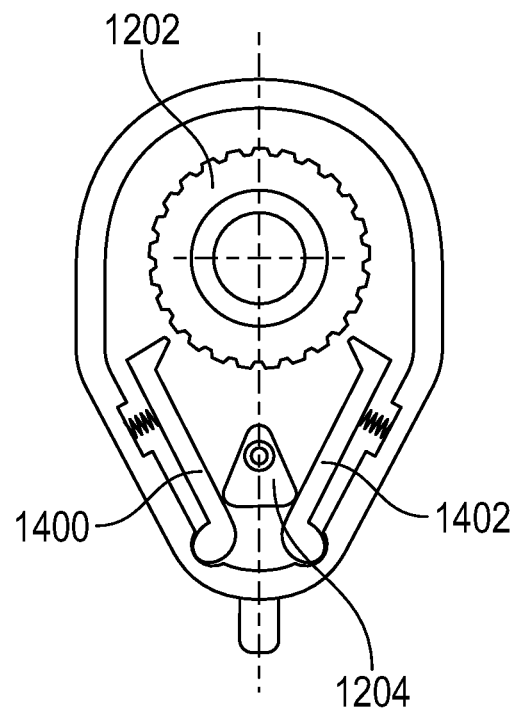

In the embodiment shown with reference to FIG. 12, the handpiece idler gear 1210 can engage with teeth 1222 of the outer flex gear 1208 and the ratchet gear 1218 via gear teeth 1224. Moreover, the outer flex gear 1208 can couple with the cutting implement 108 via the shaft 107. Thus, when a user rotates the nose cone 110, the nose cone idler gear 1212 can also rotate via the nose cone gear teeth 1214 and the nose cone idler gear teeth 1216. As the nose cone idler gear 1212 rotates, by virtue of the nose cone idler gear 1212 being operatively coupled with the handpiece idler gear 1210 via the ratchet gear 1218 and the handpiece idler gear teeth 1224, the handpiece idler gear 1210 can also rotate. Furthermore, as the handpiece idler gear 1210 rotates, by virtue of the handpiece idler gear 1210 being operatively coupled with the outer flex gear 1208 via the outer flex gear teeth 1222 and the handpiece idler gear teeth 1224, the outer flex gear 1208 can also rotate (FIG. 16A). Moreover, in the configuration shown with reference to FIG. 12, as the outer flex gear 1208 rotates, the actuator 1202 can also rotate.

Since the outer flex gear 1208 couples with the cutting implement 108, as the outer flex gear 1208 rotates, the cutting implement 108 also rotates. Therefore, when the cutting implement 108 rotates, the articulator 1202 also rotates. As noted above, the ratchet control assembly 1200 can be used to articulate the distal end of the handheld surgical instrument 100 via the articulation portion 112. However, when the articulator 1202 rotates with the cutting implement 108, articulation of the distal end of the handheld surgical instrument 100 via the articulation portion 112 may not occur.

Figure 13:
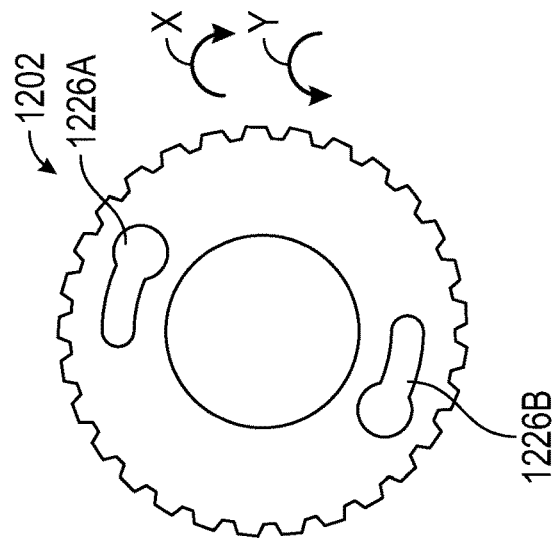

In order to facilitate articulation, the ratchet control assembly 1200 operatively cooperates with the flat pull wires 208. In particular, as shown with reference to FIGS. 12 and 13, the flat pull wires 208 can feed through the articulator 1202 and anchor with the articulator 1202 at the proximal end of the handheld device 100 via pull wire anchors 1226A and 1226B. In an embodiment, when the articulator 1202 rotates along the direction X, the distal end of the handheld surgical instrument 100 can articulate along the direction X such that the articulation portion 112 can have positive articulation as described herein.

Figure 14:
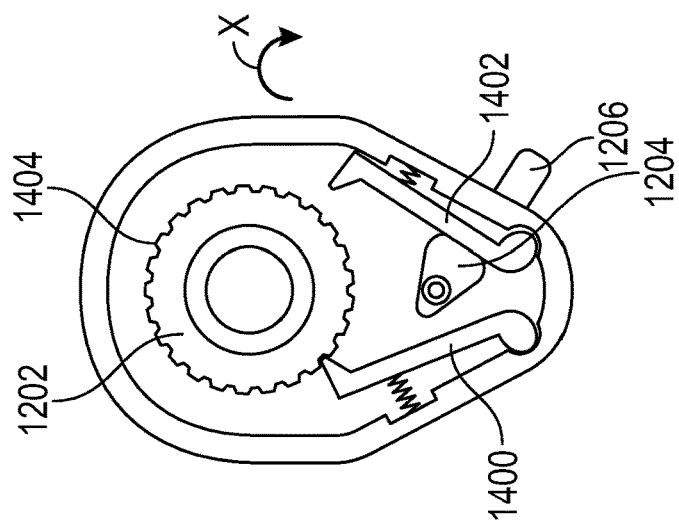

In an embodiment, in order to allow rotation of the articulator 1202 along the direction X, the ratchet control assembly 1200 can include pawls 1400 and 1402 that can engage with gear teeth 1404 of the articulator 1202, as shown with reference to FIG. 14. In the embodiment shown with reference to FIG. 14, when the articulator 1202 rotates in the direction X, in order to allow articulation of the distal end of the handheld device 100, the pawl 1400 engages with the ratchet gear teeth 1404 while the pawl 1402 disengages with the ratchet gear teeth 1404. In an embodiment, the pawl 1400 can be caused to engage with the ratchet gear teeth 1404 by moving the cam 1204 via the switch lever 1206 into the configuration shown with reference to FIG. 14. In an embodiment, when the cam 1204 is moved into the position shown with reference to FIG. 14, the handpiece idler gear 1210 disengages from the outer flex gear 1208 such that when the nose cone 10 is rotated, the outer flex gear 1208 may not rotate, such that the cutting implement 108 also does not rotate. In order to rotate the articulator 1202 along the direction X, a user can rotate the nose cone 110 along the direction X. As the user rotates the nose cone 110 along the direction X, the nose cone idler gear 1212 can be rotated via the nose cone gear teeth 1214 and the nose cone idler gear teeth 1216. As the nose cone idler gear teeth 1216 rotate, the nose cone idler gear teeth 1216 can rotate the ratchet gear teeth 1218, thereby rotating the articulator 1202 along the direction X. In particular, by virtue of the pawl 1402 being spaced away from the articulator 1202 and not in contact with the articulator 1202, the articulator 1202 can rotate in the direction X. Moreover, when the pawl 1400 is in the configuration shown with reference to FIG. 14, since the outer flex gear 1208 is disengaged from the handpiece idler gear 1210, the outer flex gear 1208 along with the cutting implement 108 may not rotate. In an embodiment, since only the articulator 1202 and the flat pull wire 208 rotate, the flat pull wire 208A can be pulled along the direction A while the flat pull wire 208B can be pushed along the direction B. As the flat pull wire 208A is pulled along the direction A and the pull wire B is pushed along the direction B, the distal end of the handheld surgical instrument 100 can articulate via the articulation portion 112 such that the articulation portion 112 can have positive articulation as described herein.

Figure 15:
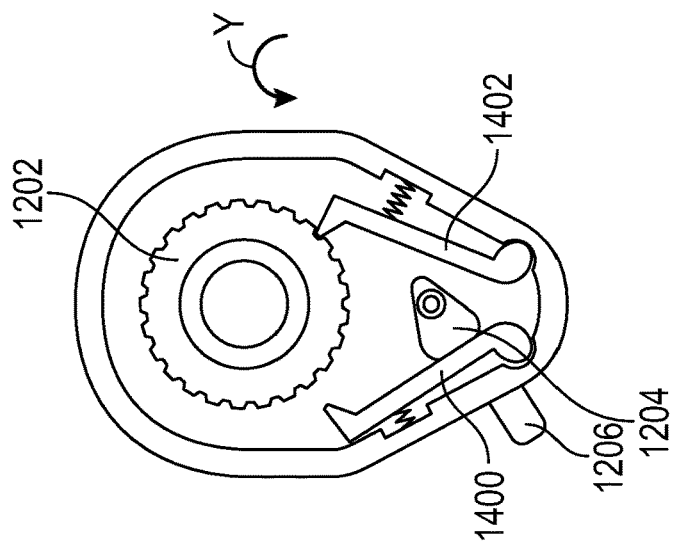
FIGS. 13-16B illustrate a functioning of a ratchet assembly of the articulation control assembly of FIG. 12 in accordance with at least one example of the present disclosure.

Returning attention to FIGS. 12 and 13, when the articulator 1202 rotates along the direction Y, the distal end of the handheld surgical instrument 100 can articulate along the direction Y such that the cutting implement 108 can have negative articulation as described herein. In an embodiment, in order to allow rotation of the articulator 1202 along the direction Y, the pawl 1402 can engage with ratchet gear teeth 1404, as shown with reference to FIG. 15. In the embodiment shown with reference to FIG. 15, when the articulator 1202 rotates in the direction Y, in order to articulate the distal end of the handheld device 100, the pawl 1402 engages with the ratchet gear teeth 1404 while the pawl 1400 disengages with the ratchet gear teeth 1404. In an embodiment, by virtue of the pawl 1400 being spaced away from the articulator 1202 and not in contact with the articulator 1202, the articulator 1202 may rotate in the direction Y. In an embodiment, the pawl 1402 can be caused to engage with the ratchet gear teeth 1404 by moving the cam 1204 via the switch lever 1206 into the configuration shown with reference to FIG. 15. In an embodiment, when the cam 1204 is moved into the position shown with reference to FIG. 15, the handpiece idler gear 1210 disengages from the outer flex gear 1208 such that when the nose cone 10 is rotated, the outer flex gear 1208 may not rotate, such that the cutting implement 108 also does not rotate. In order to rotate the articulator 1202 along the direction Y, a user can rotate the nose cone 110 along the direction Y. As the user rotates the nose cone 110 along the direction Y, the nose cone idler gear 1212 can be rotated via the nose cone gear teeth 1214 and the nose cone idler gear teeth 1216. As the nose cone idler gear teeth 1216 rotate, the nose cone idler gear teeth 1216 rotate the ratchet gear teeth 1218, thereby rotating the articulator 1202 along the direction Y. By virtue of the pawl 1400 being spaced away from the articulator 1202 and not in contact with the articulator 1202, the articulator 1202 may rotate in the direction Y. Moreover, when the pawl 1402 is in the configuration shown with reference to FIG. 15, since the outer flex gear 1208 is disengaged from the handpiece idler gear 1210, the outer flex gear 1208 along with the cutting implement 108 may not rotate. In an embodiment, since only the articulator 1202 and the flat pull wire 208 rotate, the flat pull wire 208A is pushed along the direction B while the flat pull wire 208B is pulled along the direction A. As the flat pull wire 208A is pushed along the direction B and the pull wire B is pulled along the direction A, the articulation portion 112 can move such that the articulation portion 112 can have negative articulation as described herein.

Figure 16B:
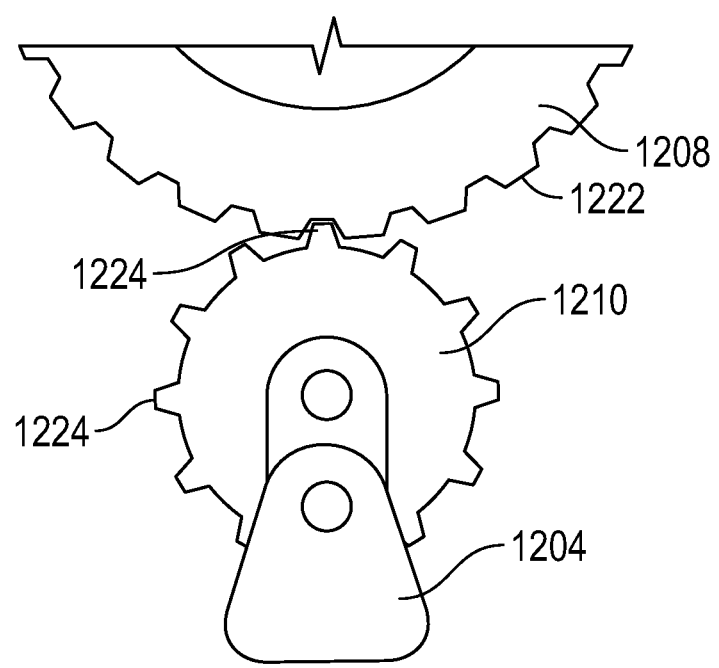

Moreover, in an embodiment, both of the pawls 1400 and 1402 are disengaged with the articulator 1202 as shown with reference to FIGS. 16A and 16B. In this embodiment, when each of the pawls 1400 and 1402 are disengaged, the cam 1204 has the position shown with reference to FIG. 16B, such that the handpiece idler gear 1210 engages with the outer flex gear 1208 such that the articulator 1202 rotates with the outer flex gear 1208. When the articulator 1202 rotates with the outer flex gear 1208 and the cutting implement 108, articulation of the articulation portion 112 does not occur since the pull wires 208A and 208B do not move in the directions A and B.

Figure 17:
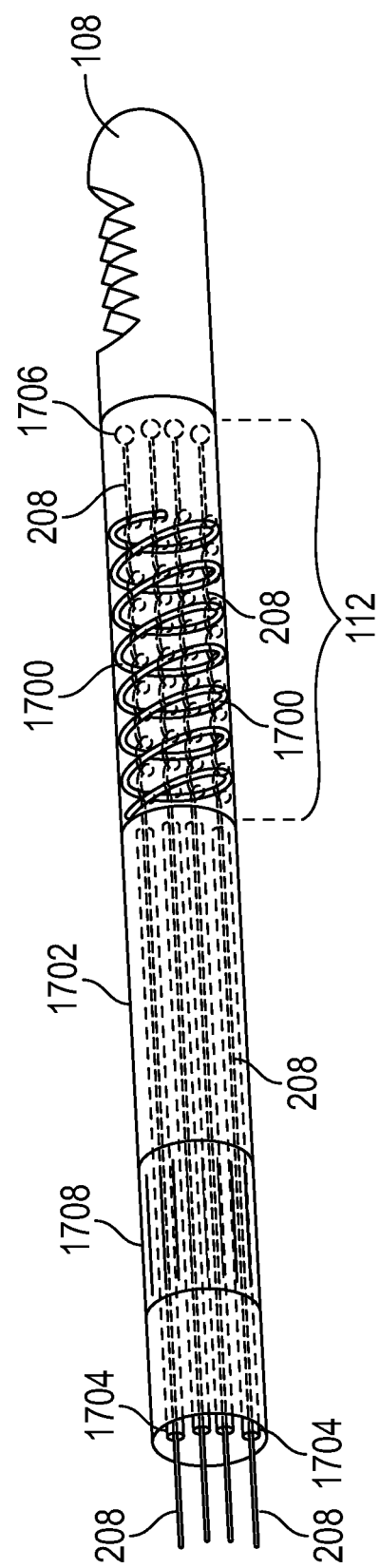
FIGS. 17-25 illustrate alternative embodiments of the articulation portion of FIG. 2 in accordance with at least one example of the present disclosure.

As described above, the articulation portion 112 can include slits 200 and 202 configured to facilitate articulation of the cutting implement 108. In accordance with a further embodiment, the articulation portion 112 can include alternative configurations that can allow for articulation of the cutting implement 108. For example, FIG. 17 shows an embodiment where the articulation portion 112 can include compressible springs 1700 where the flat pull wires 208 are disposed within coils of the compressible springs 1700. In an embodiment, the hypotube 1700 may be formed from any rigid material, such as metal, plastic, or the like. In this embodiment, the handheld surgical instrument 100 includes a hypotube section 1702 having passageways 1704 disposed therein through which the flat pull wires 208 may pass from a proximal end of the handheld surgical instrument 100 to the distal end of the handheld surgical instrument 100. In an embodiment, the articulation portion 1700 may include pull wire anchor points 1706. In an embodiment, the flat pull wires 208 may anchor with the cutting implement 108 at the anchor points 1700 with soldering, spot welding, threaded fasteners, rivets, or the like. Furthermore, the flat pull wires 208 can be anchored to the cutting implement 108 at the anchoring area with an adhesive, such as an epoxy, a glue, or the like. The embodiments shown with reference to FIG. 17 can be used with the articulation control assembly 800 or the ratchet control assembly 1200 such that either of the assemblies 800 or 1200 may be used to articulate the cutting implement 108 using the articulation portion 112 described with reference to FIG. 17. Moreover, in an embodiment, a heat shrink outer tube 1708 may be disposed about an outer periphery of the hypotube section 1702. While the heat shrink outer tube 1708 is shown covering a portion of the hypotube section 1702, the heat shrink outer tube 1708 can be configured to completely cover the hypotube section 1702.

Figure 18:
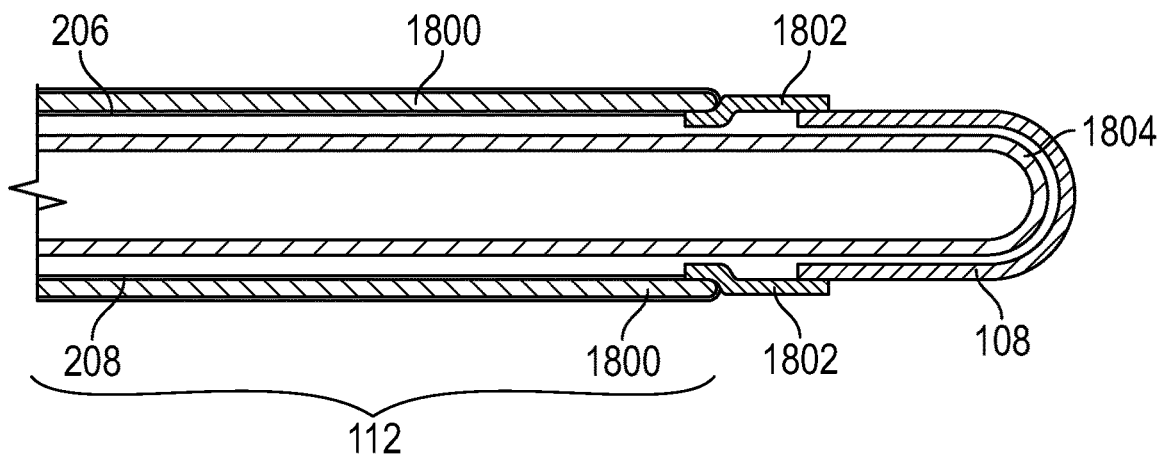
Figure 19:
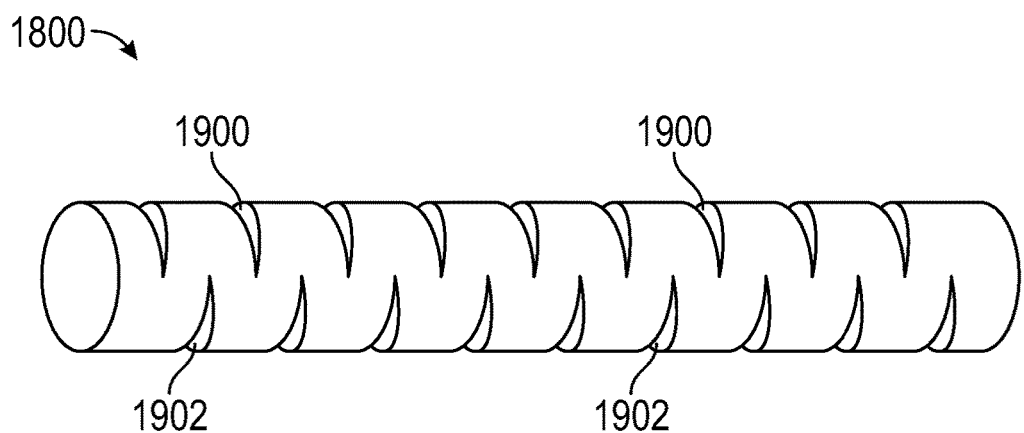
Figure 20:
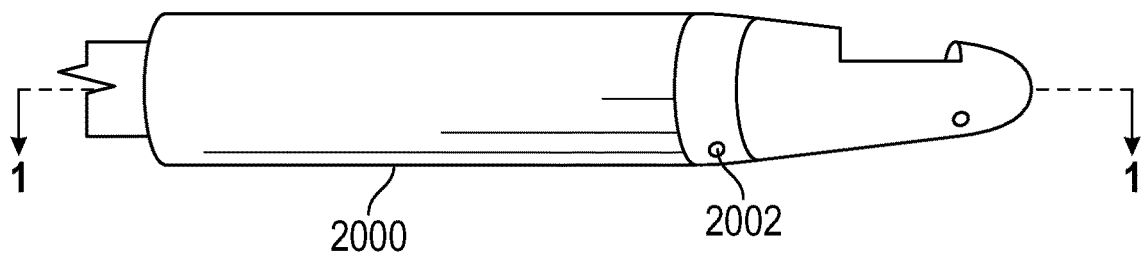

In addition to the embodiment shown with regards to FIG. 17, the articulation portion 112 can also have the configuration shown with reference to FIGS. 18-20. In the embodiment shown with regards to FIG. 18, the articulation portion 112 can include a tube 1800 that can include slots 1900 and 1902 (FIG. 19), where the slots 1900 and 1902 are configured to allow for positive and negative articulation of the cutting implement 108 as discussed herein and with reference to FIGS. 4A and 4B. As may be seen with reference to FIG. 19, the slots 1900 are disposed on a first side of the tube 1800 while the slots 1902 are disposed on a second side of the tube opposite the slots 1900. Moreover, as may be seen with reference to FIG. 19, the slots 1900 are offset from the slots 1902.

In an embodiment, the flat pull wires 208 may be disposed at an inner portion of the tube 1800 and couple with anchor rings 1802. The anchor rings 1802 can be standoffs disposed at the cutting implement 108. In an embodiment, the anchor rings 1802 can include an annular stand-off, similar to a bearing, to support and center the rotating blade 1804. Moreover, the anchor rings 1802 serve to anchor the pull wires disclosed herein and also to support or center or support and center the cutting blades disclosed herein. Furthermore, the anchor ring 1802 can be fully annular or interrupted. In an embodiment, the anchor rings 1802 can interface with the cutting implement 108 with soldering, spot welding, threaded fasteners, rivets, or the like. Furthermore, the anchor rings 1802 can interface with the cutting implement 108 at the anchoring area with an adhesive, such as an epoxy, a glue, or the like. Likewise, the flat pull wires 208 can anchor with the cutting implement 108 at the anchor rings 1802 with soldering, spot welding, threaded fasteners, rivets, or the like. Furthermore, the flat pull wires 208 can be anchored to the cutting implement 108 at the anchor rings 1802 with an adhesive, such as an epoxy, a glue, or the like. In addition, a rotating blade 1804 can be disposed within the tube 1800. It should be noted that all of the embodiments disclosed herein can include the rotating blade 1804 in the configuration with reference to FIG. 18. In an embodiment when the handheld surgical instrument 100 is being used for tissue resection, the rotating blade 1804 can rotate within the tube 1800. In an embodiment, the rotating blade 1804 can include an inner blade edge (not shown), which defines an inner blade window (not shown). Moreover, the inner blade edge, in conjunction with the cutting implement 108, can be used for resection during use of the handheld surgical instrument 100. In the embodiment shown with reference to FIGS. 18-20, the tube 1800 can be covered with a heat shrink outer tube 2000 that couples with a joint 2002. In an embodiment, the joint 2002 can function to center the heat shrink outer tube 2000 over the articulation portion 112. The embodiments shown with reference to FIGS. 18-20 can be used with the articulation control assembly 800 or the ratchet control assembly 1200 such that either of the assemblies 800 or 1200 can be used to articulate the cutting implement 108 using the articulation portion 112 described with reference to FIGS. 18-20.

Figure 21:
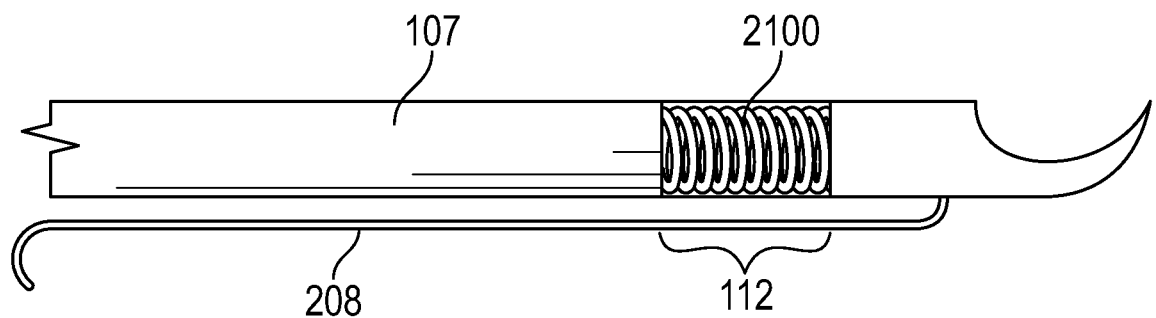
Figure 22:
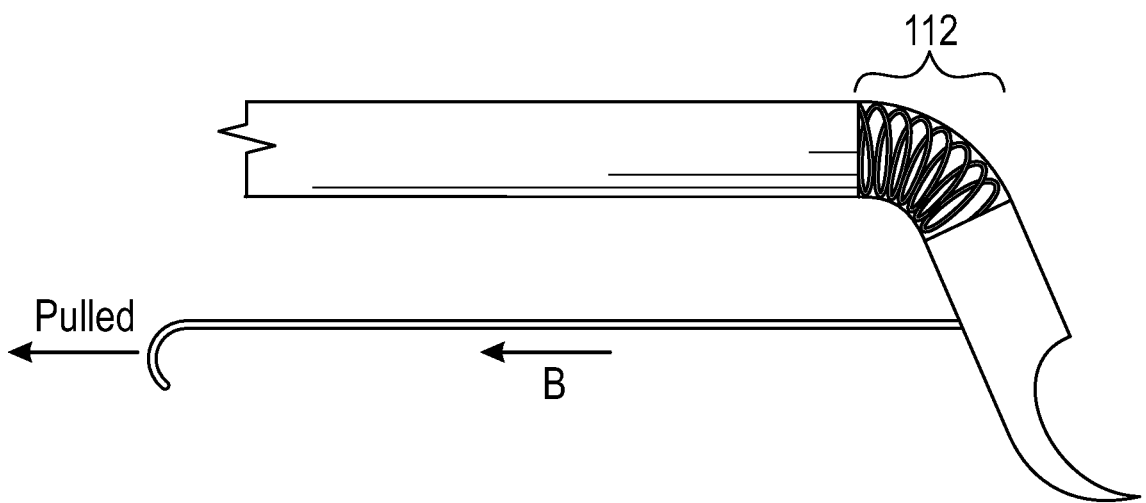
Figure 23:
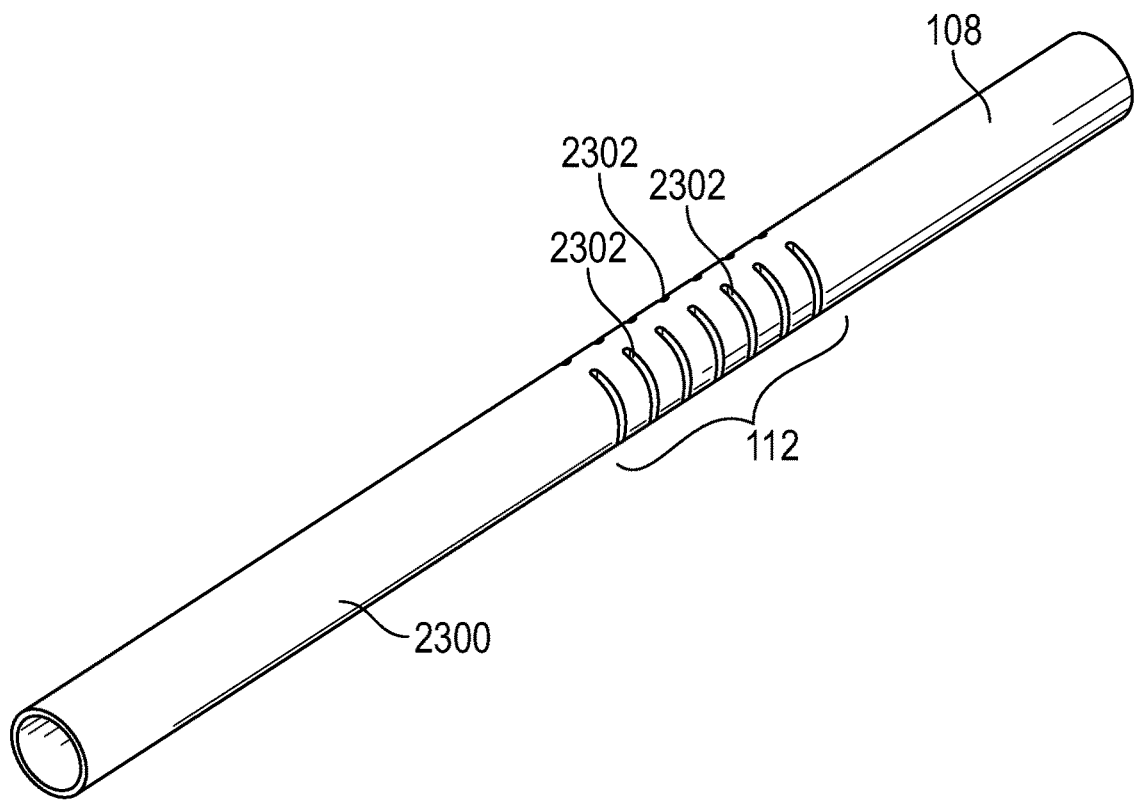
Figure 24:
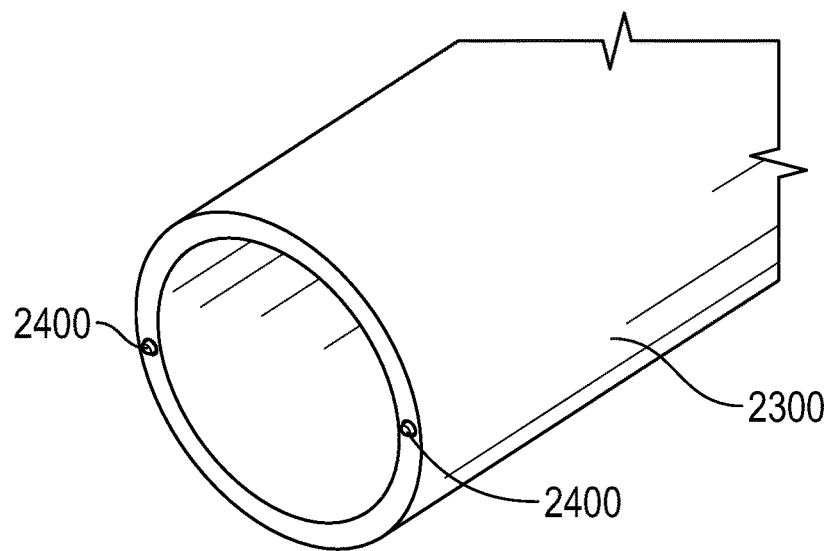
Figure 25:
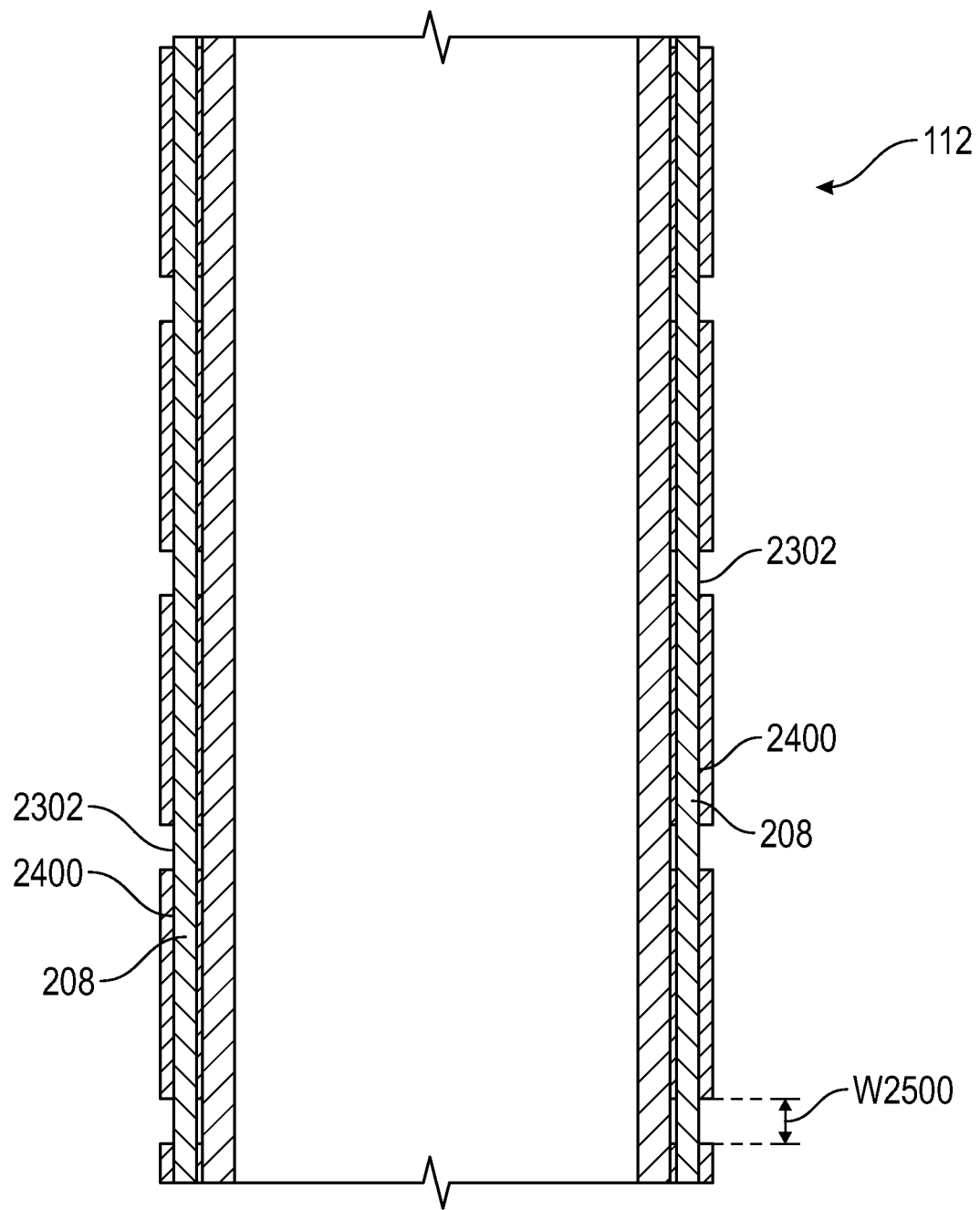

In addition to the embodiments shown with reference to FIGS. 17-20, the articulation portion 112 may have the configuration shown with reference to FIGS. 21 and 22. In this embodiment, the articulation portion 112 can include an articulation member 2100, which can be a compression spring or a semi-rigid ductile polymer, such as plastic. In this embodiment, the flat pull wire 208 is disposed at an outer surface of the shaft 107 and extends from the proximal portion of the handheld surgical instrument 100 to the cutting implement 108. The embodiments shown with reference to FIGS. 21 and 22 can be used with the articulation control assembly 800 or the ratchet control assembly 1200 such that either of the assemblies 800 or 1200 can be used to articulate the cutting implement 108 using the articulation portion 112 described with reference to FIGS. 21 and 22. Thus, in an embodiment, either of the assemblies 800 and 1200 can be used to control the flat pull wire 208 such that the articulation member 2100 articulates as shown with reference to FIG. 21. More specifically, the flat pull wire 208 may be pulled along the direction B, thereby causing the cutting implement 108 to articulate as shown with reference to FIG. 22. In some embodiments, the pull wire 208 can be inside the tube 107 or between the tube 107 and another tube disposed about the tube 107.

In addition to the embodiments discussed above, the cutting implement 108 can be articulated in accordance with embodiments disclosed with references to FIGS. 23-33. Now making reference to FIG. 23, an alternative embodiment of the articulation portion 112 is shown. In this embodiment, the articulation portion 112 can be disposed on a shaft 2300 and can include slits 2302. In an embodiment, the slits 2302 can allow for flexing of the articulation portion 112 thereby allowing positive and negative articulation of the cutting implement 108, as discussed herein and shown with reference to FIGS. 4A and 4B. In particular, the shaft 2300, along with the articulation portion 112, can include passageways 2400 that are configured to receive the flat pull wires 208, as shown with regards to FIGS. 24 and 25. Therefore, using the flat pull wires 208, the cutting implement 108 can be articulated such that the cutting implement 108 can have positive articulation as described herein. Moreover, using the flat pull wires 208, the cutting implement 108 can be articulated from a curved position such that the cutting implement 108 can have negative articulation as described herein. In an embodiment, the flat pull wires 208 can be controlled with the articulation control assembly 800 or the ratchet control assembly 1200 discussed above.

In an embodiment, the slits 2302 can be configured to allow articulation of the cutting implement 108 as discussed above. In an embodiment, the slits 2302 can have a width $W_{2500}$ that can be in a range of about 0.0038 inches to about 0.0046 inches. In an embodiment, the slits 2302 can have a width $W_{2500}$ that can be in a range of about 0.005 inches to about 0.150 inches. In an embodiment, by virtue of the slits 2302 having the width $W_{2500}$, the slits 2302 can allow articulation of the articulation portion 112.

Figure 26:
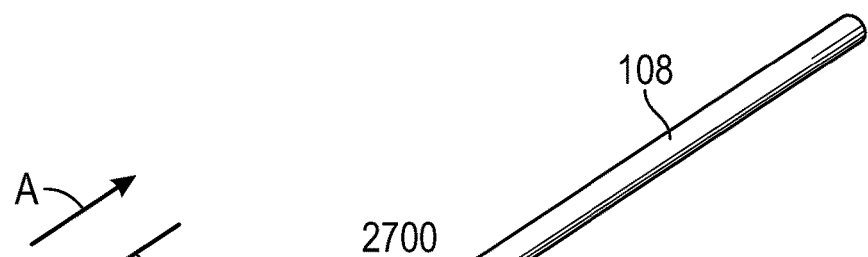
FIGS. 26-33 illustrate alternative embodiments of the articulation portion of FIG. 2 in accordance with at least one example of the present disclosure.
Figure 27:
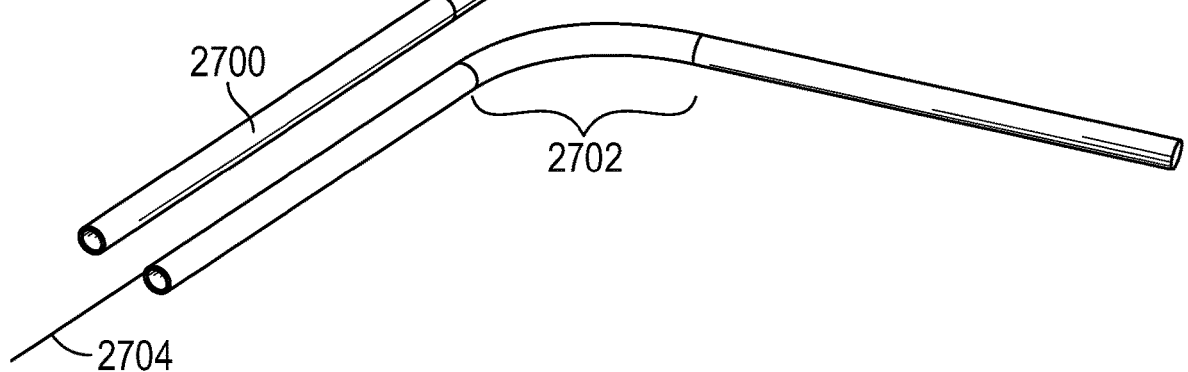

Now making reference to FIGS. 26 and 27, further methods of articulating the cutting implement 108 are shown in accordance with an alternative embodiment of the present disclosure. In accordance with an embodiment, the handheld surgical instrument 100 can include a shaft 2700 that can include an articulation portion 2702, as shown with reference to FIGS. 26 and 27. In an embodiment, each of the shaft 2700 and the articulation portion 2702 can be formed of a semi-rigid material that is bendable. Examples of a material that can be used for the each of the shaft 2700 and the articulation portion 2702 can include stainless spring steel, plastic, a shape-memory material, such as nitinol or super-elastic nitinol, or any other type of polymer having bendable properties. In an embodiment, the cutting implement 108 can be disposed at a distal end of the shaft 2700 such that when the handheld surgical device 100 includes the shaft 2700 and the articulation portion 2702, the handheld surgical device 100 can be used for tissue resection, as discussed above.

Figure 28:
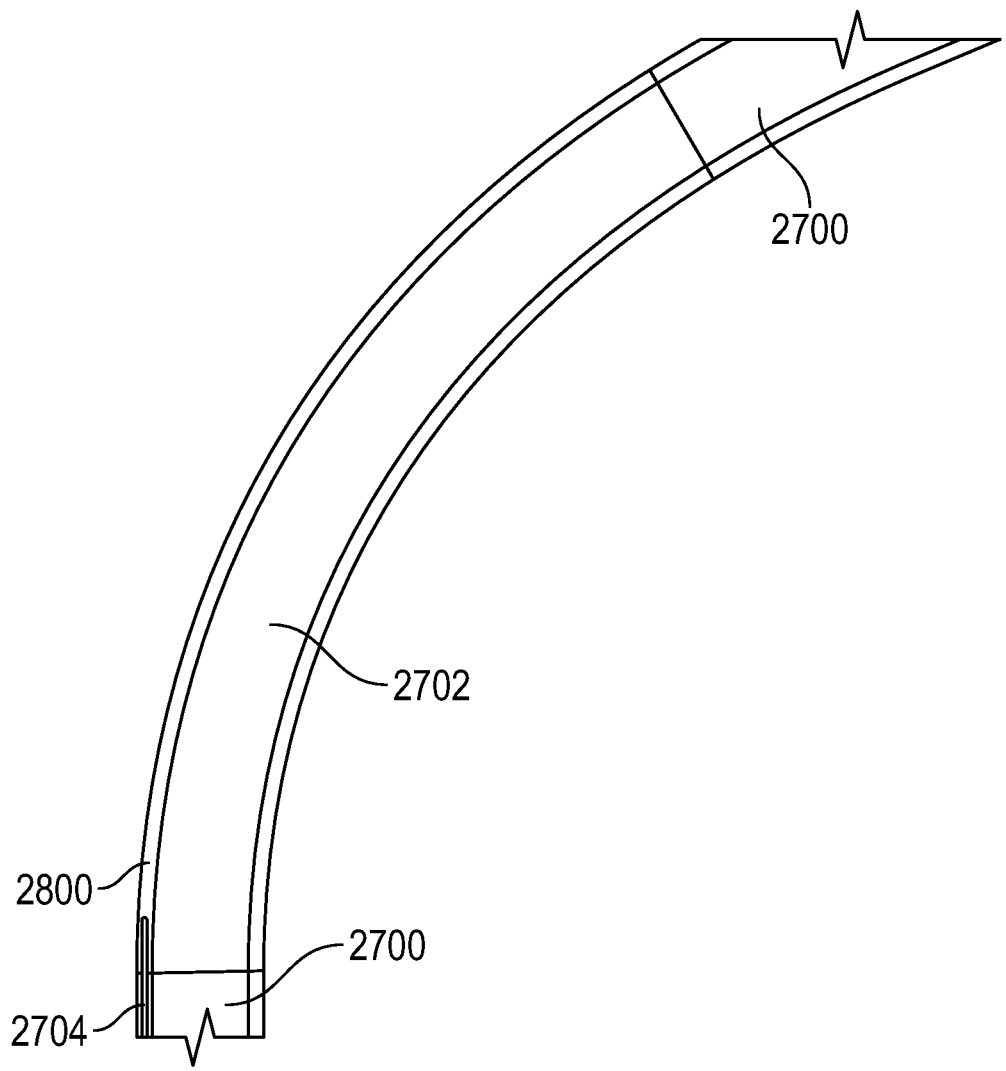
Figure 29:
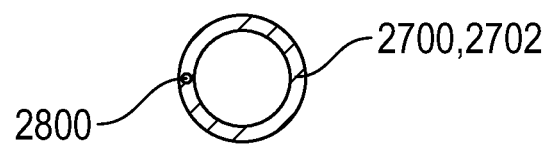

In the embodiment shown with regards to FIGS. 26 and 27, an articulating shaft 2704 may be inserted into a passageway 2800 (FIGS. 28 and 29). In an embodiment, the articulating shaft 2704 may be formed of a rigid a material, including a metal alloy such as steel or aluminum, a rigid polymer, or the like, and may traverse portions of both the shaft 2700 and the articulation portion 2702. In an embodiment, due to the rigidity of the articulating shaft 2704, when the articulating shaft 2704 completely traverses the articulation portion 2702 via the passageway 2800 in a first position, the shaft 2700 and the articulation portion 2702 have a substantially straight configuration, as shown with reference to FIG. 26. Here, a natural position of the articulation portion 2702 may be in a bent configuration as shown with reference to FIG. 27. Thus, when the articulating shaft 2704 is removed from the articulation portion 2702 in a second position, the articulation portion 2702 can have the bent configuration as shown with reference to FIG. 27. When the articulating shaft 2700 traverses the articulation portion 2702, either completely or partially, the articulating shaft 2700 can cause the articulation portion 2702 to have a straight configuration as shown with regards to FIG. 26. Moreover, the articulating shaft 2700 can be moved in the direction A or the direction B such that the cutting implement 108 can move from the substantially curved position shown with reference to FIGS. 4A and 4B towards a position that is less curved than either of the positions shown with reference to FIGS. 4A and 4B. It should be noted that articulation is not limited to what is shown with reference to FIGS. 4A and 4B. In particular, the distal end of the handheld surgical instrument 100 can articulate via the articulation portion 112 such that there is more or less articulation that is shown with reference to FIGS. 4A and 4B. In addition, using the articulating shaft 2700, the cutting implement 108 can be moved from a substantially flat position to one of the positions shown with reference to FIGS. 4A and 4B where the articulating shaft can be moved along the direction A.

In an embodiment, the articulating shaft 2704 can be connected to a control assembly, such as the articulation control assembly 800 or the ratchet control assembly 1200 discussed above. In an embodiment, a proximal end of the articulating shaft 2704 can be coupled to the flat pull wire 208 and can be controlled via the articulation control assembly 800. In this embodiment, only a single flat pull wire 208, such as the flat pull wire 208A, would be used with the articulation control assembly 800 since articulation of the shaft 2700 and the articulation portion 2702 are controlled with a single implement, the articulation shaft 2704. For example, the articulation control assembly 800 would only include the flat pull wire 208A where the articulation control assembly 800 only controls the flat pull wire 208A as discussed above. Moreover, in this embodiment, only a single flat pull wire 208, such as the flat pull wire 208A, would be used with the ratchet control assembly 1200 since articulation of the shaft 2700 and the articulation portion 2702 are controlled with a single implement, the articulation shaft 2404. For example, the articulation control assembly 1200 would only include the flat pull wire 208A where the articulation control assembly 1200 only controls the flat pull wire 208A as discussed above. A rack-and-pinion system may also be used to control movement of the articulating shaft 2704, in accordance with an embodiment.

Figure 30:
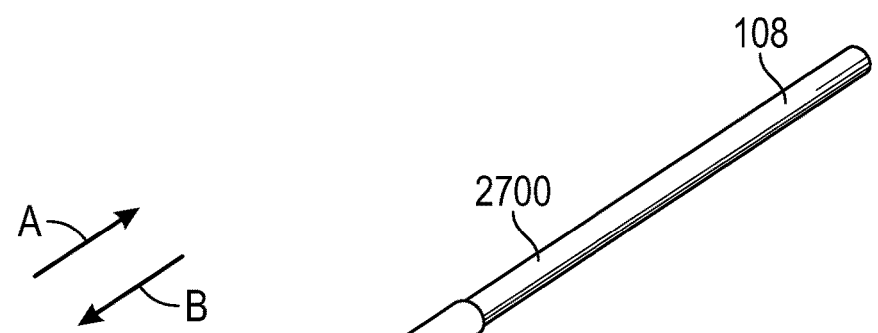
Figure 31:
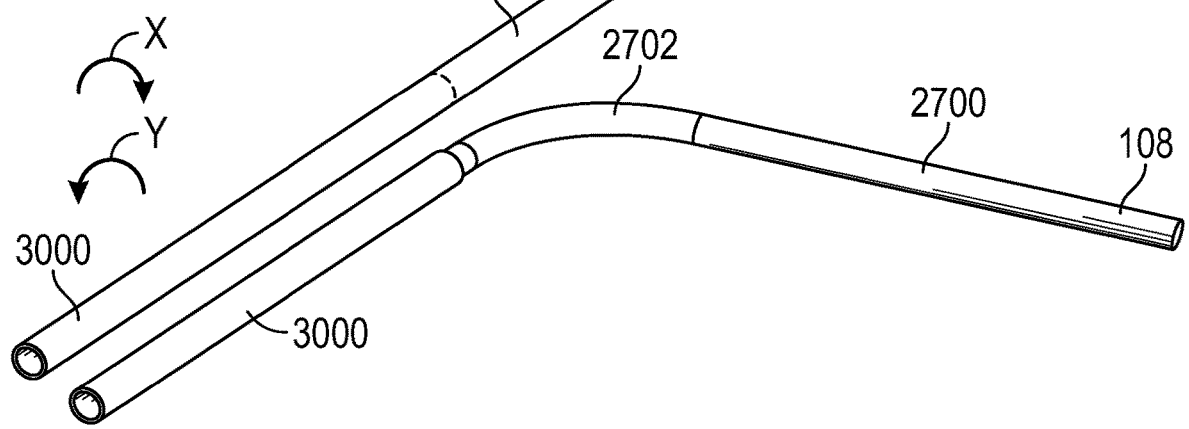
Figure 32:
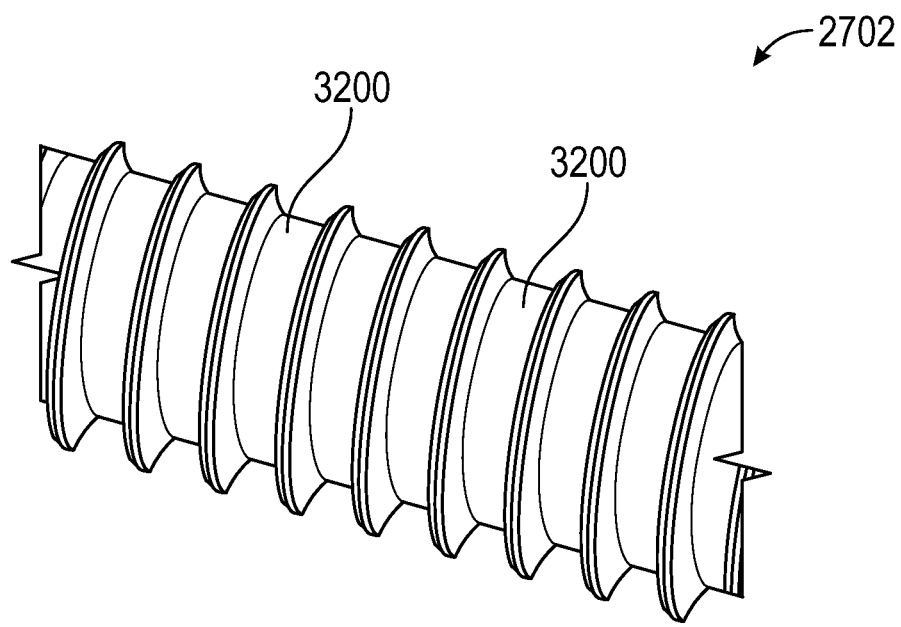
Figure 33:
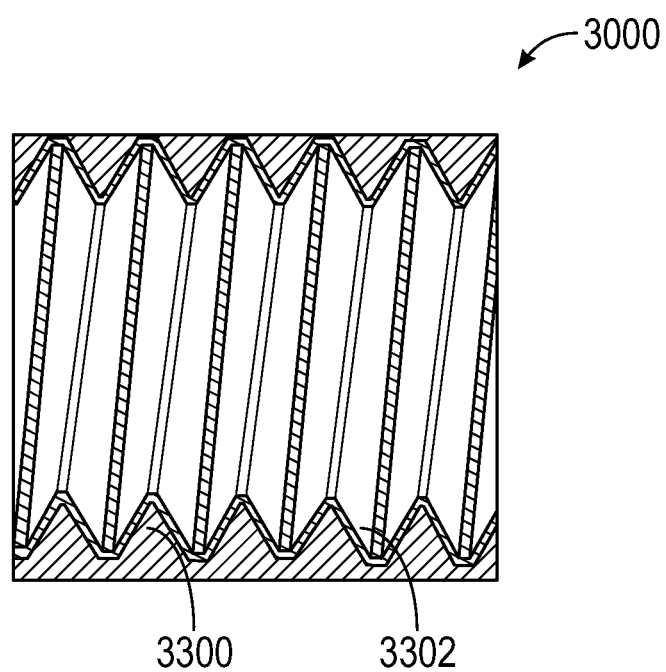

Now making reference to FIGS. 30 and 31, further methods of articulating the cutting implement 108 are shown in accordance with an alternative embodiment of the present disclosure. The handheld surgical instrument 100 can include the shaft 2700 and the articulating portion 2702 along with a straight tube 3000. The straight tube 3000 can be formed of any rigid material. Examples can include any type of metal alloy, such as stainless steel or aluminum or the like, or any rigid polymer. In an embodiment, due to the rigidity of the straight tube 3000, when the straight tube 3000 completely traverses or partially traverses the articulation portion 2702, the shaft 2700 and the articulation portion 2702 have a substantially straight configuration, as shown with reference to FIG. 30. Here, a natural position of the articulation portion 2702 may be in a bent configuration as shown with reference to FIG. 31 and discussed above. When the straight tube 3000 traverses the articulation portion 2702, either completely or partially, the straight tube 3000 can cause the articulation portion 2702 to have a straight configuration in a first position as shown with regards to FIG. 30.

In an embodiment, the straight tube 3000 can slidingly engage with the shaft 2700 and the articulation portion 2702 such that a user can slide the straight tube 3000 along the directions A and B. In an embodiment, when a user slides the straight tube 3000 along the direction B from the configuration shown with respect to FIG. 30, the cutting implement 108 may articulate into the configuration in a second position shown with reference to FIG. 31. Furthermore, the straight tube 3000 can be moved in the direction A or the direction B such that the cutting implement 108 can move from the substantially curved position shown with reference to FIGS. 4A and 4B towards a position that is less curved than either of the positions shown with reference to FIGS. 4A and 4B. It should be noted that articulation is not limited to what is shown with reference to FIGS. 4A and 4B. In particular, the distal end of the handheld surgical instrument 100 can articulate via the articulation portion 112 such that there is more or less articulation that is shown with reference to FIGS. 4A and 4B. In an embodiment, the straight tube 3000 can include a knob that can allow for movement of the straight tube 3000 along the directions A and B. In addition, using the straight tube 3000, the cutting implement 108 can be moved from a substantially flat position to one of the positions shown with reference to FIGS. 4A and 4B, where the straight tube 3000 can be moved along the direction A.

Additionally, the straight tube 3000 can threadingly engage with the articulation portion 2702. In particular, the articulation portion 2702 can include threads 3200 (FIG. 32) disposed about an outer surface of the articulation portion 2702. In this embodiment, the straight tube 3000 can include threads 3300 (FIG. 33) disposed at an inner surface thereof that complement the articulation portion threads 3200. In this configuration, a user can rotate the straight tube 3000 along the direction A or the direction Y. In an embodiment, when a user twists the straight tube 3000 along the direction X, the straight tube moves along the direction A. In an embodiment, when a user twists the straight tube 3000 along the direction Y, the straight tube moves along the direction B. Therefore, a user may control articulation of the cutting implement 108 by twisting the straight tube 3000 in either the direction X or the direction Y. In an embodiment, the straight tube 3000 can include a knob that can allow for twisting the straight tube along the directions X and Y.

As discussed above, during articulation of the cutting implement 108, the flat pull wires 208 can be controlled with the articulation control assembly 800 or the ratchet control assembly 1200. The flat pull wires 208 may also be controlled with other assemblies, as shown with reference to FIGS. 34-40. Making reference to FIG. 34, an articulation control assembly 3400 is shown in accordance with an embodiment of the present disclosure. In an embodiment, the articulation control assembly 3400 can include an articulator 3402 disposed about a pivot 3404 and can be disposed within the handpiece 102. The articulator 3402 can couple with an actuator mechanism 3406 via a biasing mechanism neck 3408, as shown with reference to FIG. 34. The actuating mechanism 3406 can include an actuator 3410 operatively coupled with a locking mechanism 3412 via an actuator neck 3414.

In an embodiment, the flat pull wires 208A and 208B couple with the articulator 3402 at anchor points 3416. In an embodiment, the flat pull wires 208A and 208B may anchor with the anchor points 3416 at an anchoring area 3418 with soldering, spot welding, threaded fasteners, rivets, or the like. In an embodiment, the articulator 3402 is configured to rotate about the biasing mechanism pivot 3404 along the directions X and Y. In an embodiment, when the articulator 3402 rotates about the biasing mechanism pivot 3404 along the direction Y, the articulator 3402 rotates the flat pull wires 208A and 208B along the direction Y. More specifically, as the articulator 3402 rotates along the direction Y, the pull wire 208A moves along the direction B and the pull wire 208B moves along the direction A.

In an embodiment, when the articulator 3402 rotates along the direction Y, the articulator 3402 can rotate the flat pull wires 208A and 208B such that the cutting implement 108 can have positive articulation as described herein. The articulator 3402 can also rotate along the direction X about the biasing mechanism pivot 3404. When the articulator 3402 rotates along the direction X, the flat pull wires 208A and 208B can also rotate along the direction X such that the cutting implement 108 can have negative articulation as described herein.

In an embodiment, the articulator 3402 can be caused to rotate about the biasing mechanism pivot 3404 with the actuator mechanism 3406. The locking mechanism 3412 can include teeth 3420 that are configured to engage with teeth 3422 of the articulation control assembly 3400. In an embodiment, when the locking mechanism teeth 3420 are engaged with the articulation control assembly teeth 3422 as shown with reference to FIG. 34, the articulation control assembly 3400 can be in a locked position. In order to cause rotation of the articulator 3402 in either direction X or the direction Y, a user can move the actuator 3410 along a direction C such that the locking mechanism teeth 3420 are disengage with the articulation control assembly teeth 3422. Upon disengagement, the user may rotate the articulator 3402 about the biasing mechanism pivot 3404 along the direction X or the direction Y, thereby controlling articulation of the cutting implement 108.

Figure 34:
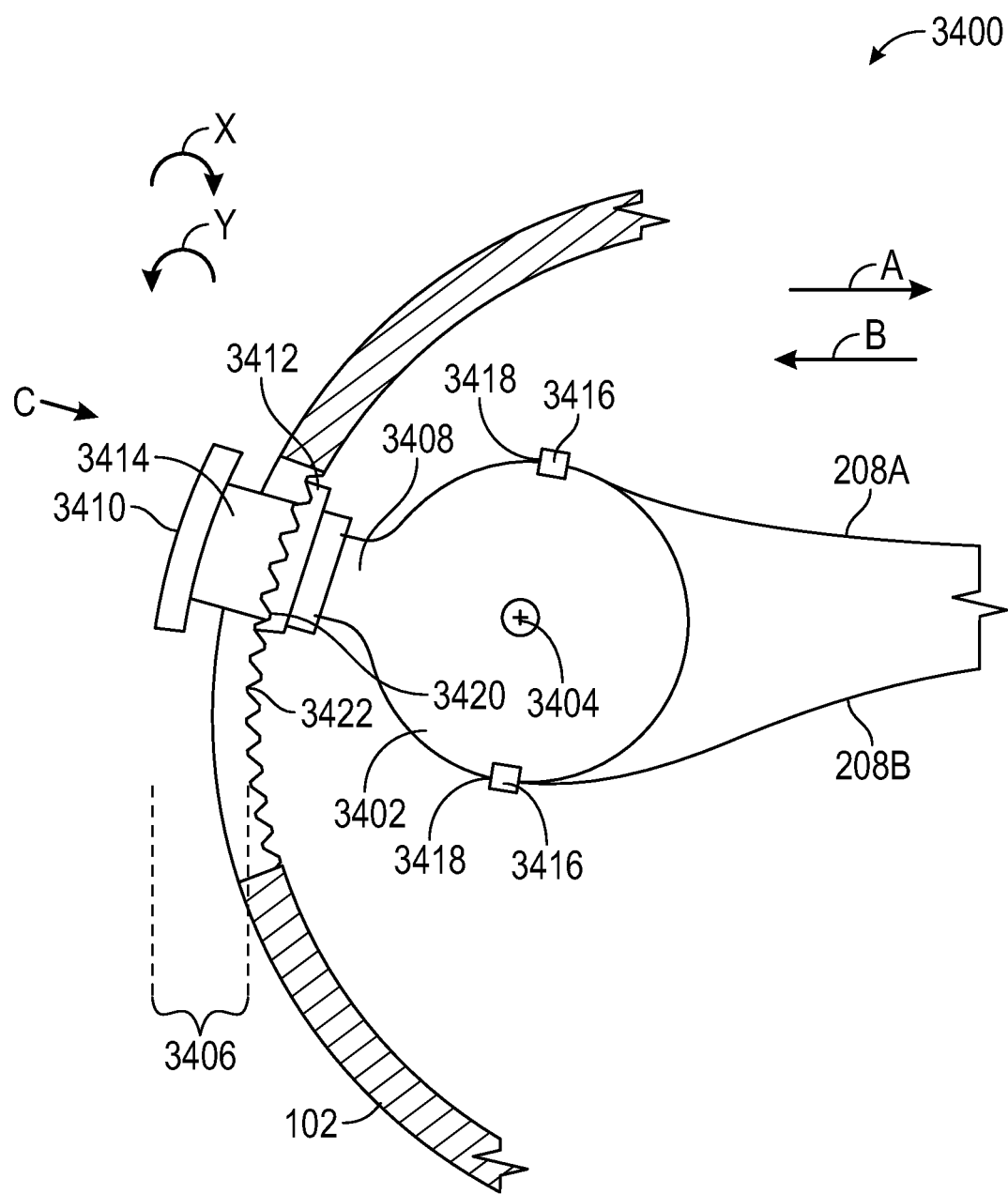
FIGS. 34-40 show alternative embodiments of articulation control assemblies that may be used with the handheld surgical instrument of FIG. 1 in accordance with at least one example of the present disclosure.
Figure 35:
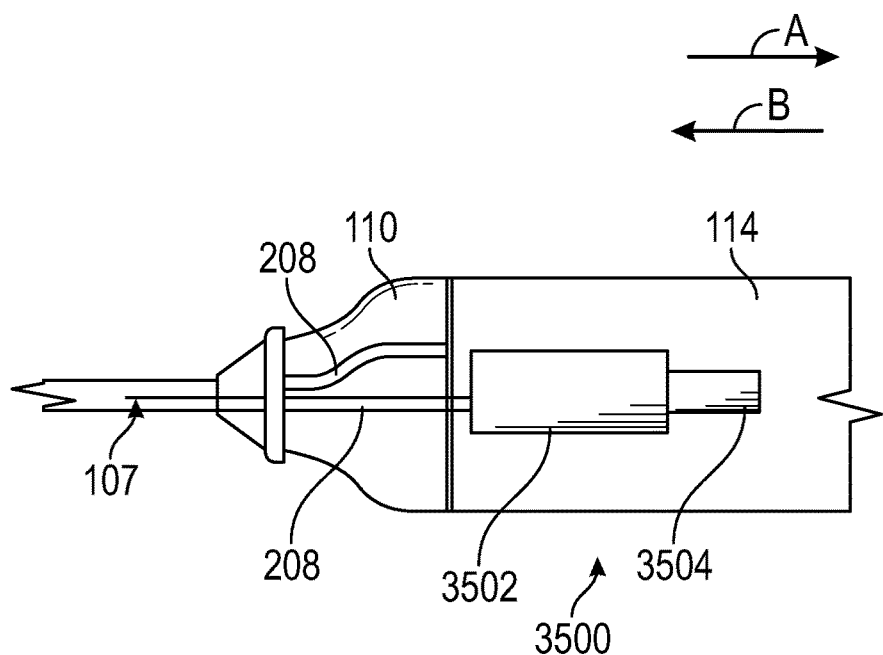
Figure 36A:
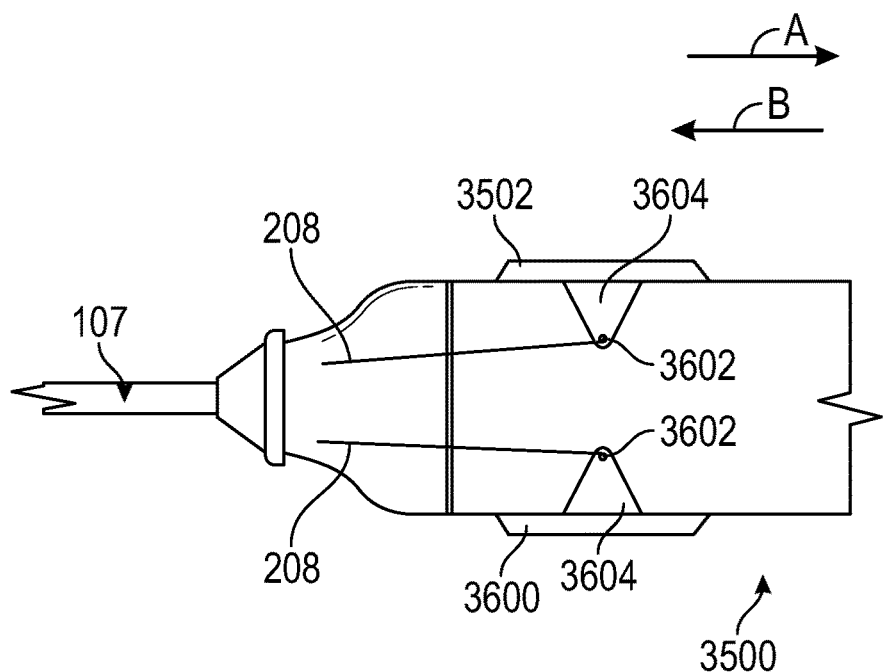

Besides the embodiment shown with reference to FIG. 34, articulation of the cutting implement 108 can be controlled via an articulation control assembly 3500 disposed within the handheld surgical instrument housing 114, as shown with respect to FIGS. 35 and 36A. In an embodiment, the articulation control assembly 3500 can include actuator slides 3502 and 3600 that are configured to slide along guides, such as a guide 3504, within the handheld surgical instrument housing 114. Each of the actuator slides 3502 and 3600 can couple with the flat pull wires 208 via anchoring points 3602 as shown with reference to FIG. 36A. In an embodiment, the flat pull wires 208 can anchor with the anchoring points 3602 at anchoring areas 3604 with soldering, spot welding, threaded fasteners, rivets, or the like.

In an embodiment, movement of the actuator slides 3502 and 3600 can cause articulation of the cutting implement 108 via the flat pull wires 208. For example, movement of the actuator slide 3502 along the direction A can cause articulation of the cutting implement 108 such that the cutting implement 108 can have positive articulation as described herein. In this example, when the movement of the actuator slide 3502 along the direction A causes positive articulation of the cutting implement 108, movement of the actuator slide 3502 along the direction B can cause articulation of the cutting implement 108 such that the cutting implement 108 can have negative articulation as described herein. Moreover, when the movement of the actuator slide 3502 along the direction A causes positive articulation of the cutting implement 108, movement of the actuator slide 3600 along the direction B can cause positive articulation of the cutting implement 108.

In addition, movement of the actuator slide 3502 along the direction A can cause articulation of the cutting implement 108 such that the cutting implement 108 can have negative articulation as described herein. In embodiments where movement of the actuator slider 3502 along the direction A causes negative articulation of the cutting implement, movement of the actuator slider 3600 along the direction B can cause articulation of the cutting implement 108 such that the cutting implement 108 can have negative articulation as described herein.

Figure 36B:
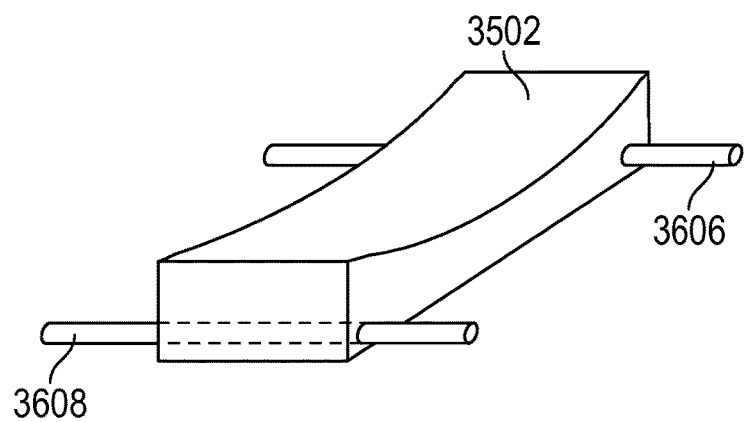
Figure 36C:
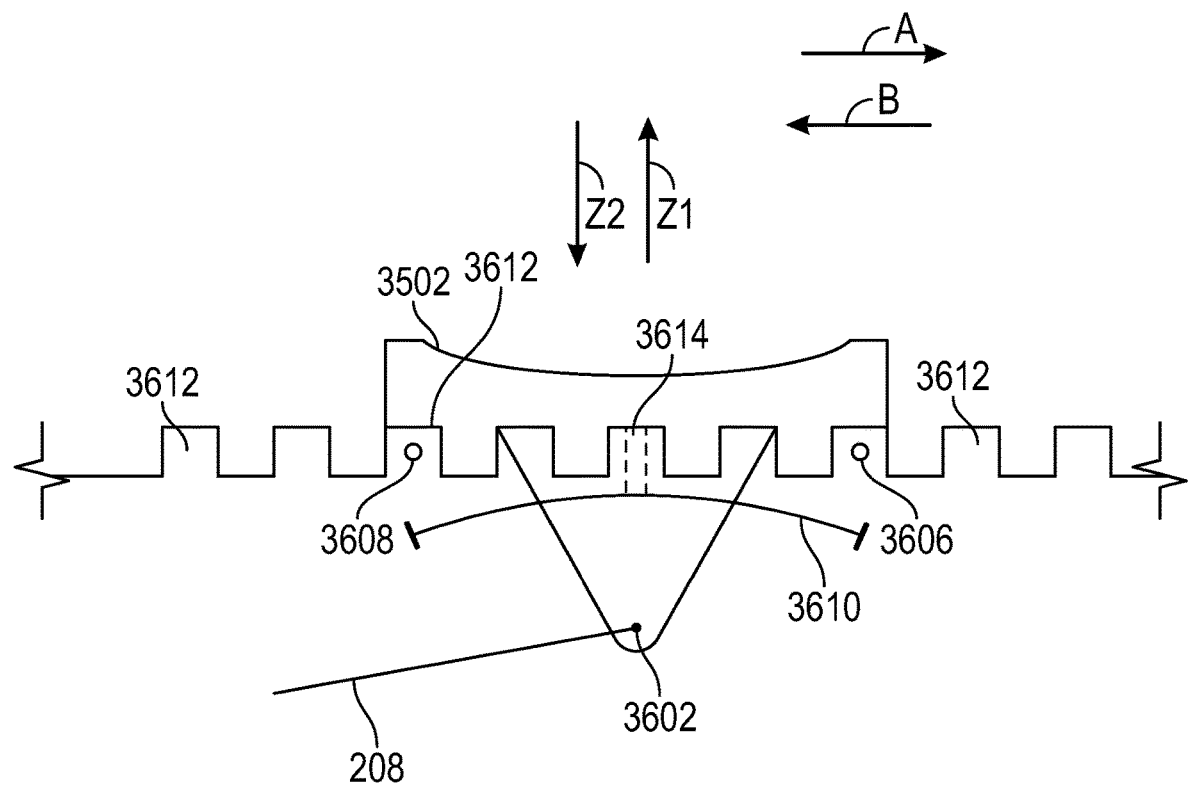

Moreover, the articulation control assembly 3500 can be secured in various positions as shown with reference to FIGS. 36B and 36C. The actuator slide 3502 can include pins 3606 and 3608 that can engage with notches 3612 of the actuator slide 3502, as shown with reference to FIGS. 36B and 36C. The articulation control assembly 3500 can include a spring 3610, such as a leaf spring, that can bias a pin 3614 that can be coupled to the articulation control assembly 3500 along a direction $Z_1$. In an embodiment, the pins 3606 and 3608 can be configured to rest within notches 3612 when the spring 3610 biases the articulation control assembly 3500 along the direction $Z_1$. When the pins 3606 and 3608 are disposed within the notches 3612, the articulation control assembly 3500 is locked into position. In order to articulate the articulation portion 112, the articulation control assembly 3500 can be moved in a direction $Z_2$, thereby moving the pins 3606 and 3608 out of the notches 3612. Moreover, the articulation control assembly can be moved along either of the directions A and B while the articulation control assembly 3500 can be moved in a direction $Z_2$. When the articulation control assembly 3500 is no longer moved in the direction $Z_2$, the spring 3610 can bias the articulation control assembly 3500 along the direction $Z_1$, whereby the pins 3606 and 3608 are moved into other notches 3612.

Figure 37A:
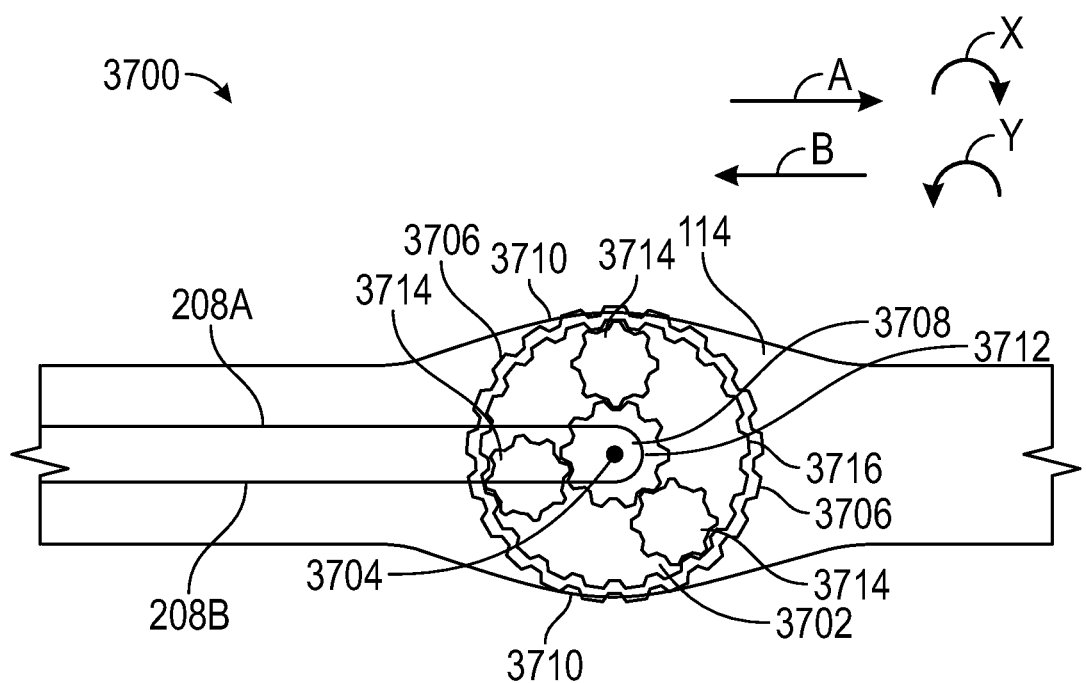
Figure 37B:
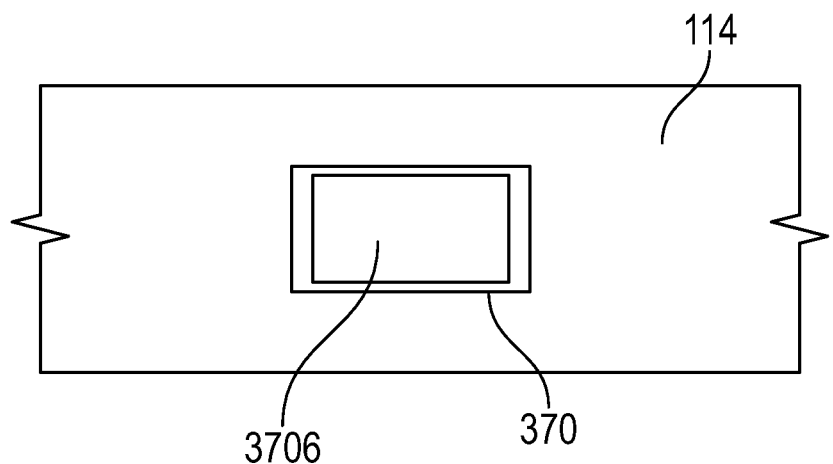

In addition to the embodiment shown with reference to FIGS. 35 and 36A, articulation of the cutting implement 108 can be controlled via an articulation control assembly 3700 disposed within the handheld surgical instrument housing 114, as shown with respect to FIGS. 37A and 37B. In an embodiment, the articulation control assembly 3700 can include an articulator 3702 disposed about a pivot 3704 along with biasing mechanism interfaces 3706 disposed about a periphery of the articulator 3702. In an embodiment, the flat pull wires 208 can couple with the articulator 3702 at an anchor point 3708. In an embodiment, the flat pull wires 208 may anchor with the anchor point 3708 with soldering, spot welding, threaded fasteners, rivets, or the like.

The biasing mechanism can be used to positively and negatively articulate the cutting implement 108. In particular, a user may rotate the articulator 3702 along either the direction X or the direction Y in order to move the pull wire wires 208A and 208B along the directions A and B. In an embodiment, the articulator 3702 can be a rotatable thumb wheel that rotates along the directions X and Y. In an embodiment, the biasing mechanism interfaces 3706 can protrude from the housing 114 at areas 3710. Thus, a user can engage the biasing mechanism interfaces 3706 at the areas 3710 and rotate the articulator 3702 along the directions X and Y. In particular, the articulation control assembly 3700 can include planetary gears 3712 and 3714 which can cooperate with each other and teeth 3716 to effectuate articulation of the articulation portion 112.

To further illustrate, in an example, rotation of the articulator 3702 along the direction X can cause movement of the flat pull wire 208A along the direction A and can cause positive articulation of the cutting implement 108 as described herein. In this example, a user may engage the biasing mechanism interfaces 3706 and rotate the articulator 3702 along the direction X. As the articulator 3702 rotates along the direction X, the flat pull wire 208A moves along the direction A while the flat pull wire 208B moves along the direction B via movement of the planetary gears 3712 and 3714. In this example, as the flat pull wire 208A moves along the direction A, the cutting implement 108 can articulate such that the cutting implement 108 can have positive articulation as described herein. Moreover, in this example, as a user rotates the articulator 3702 along the direction Y, the flat pull wire 208A moves along the direction B while the flat pull wire 208 moves along the direction A via movement of the planetary gears 3712 and 3714. Here, as the flat pull wire 208A moves along the direction B, the cutting implement 108 can articulate such that the cutting implement 108 can have negative articulation as described herein.

In a further example, movement of the flat pull wire 208A along the direction A can cause negative articulation of the cutting implement 108 as described herein. In this example, a user can engage the biasing mechanism interfaces 3706 and rotate the articulator 3702 along the direction X. As the articulator 3702 rotates along the direction X, the flat pull wire 208A moves along the direction A while the flat pull wire 208B moves along the direction B via movement of the planetary gears 3712 and 3714. In this example, as the flat pull wire 208A moves along the direction A, the cutting implement 108 can articulate such that the cutting implement 108 can have negative articulation as described herein. Moreover, in this example, as a user rotates the articulator 3702 along the direction Y, the flat pull wire 208A moves along the direction B while the flat pull wire 208 moves along the direction A. Here, as the flat pull wire 208A moves along the direction B, the cutting implement 108 can articulate such that the cutting implement 108 can have positive articulation as described herein.

Figure 38A:
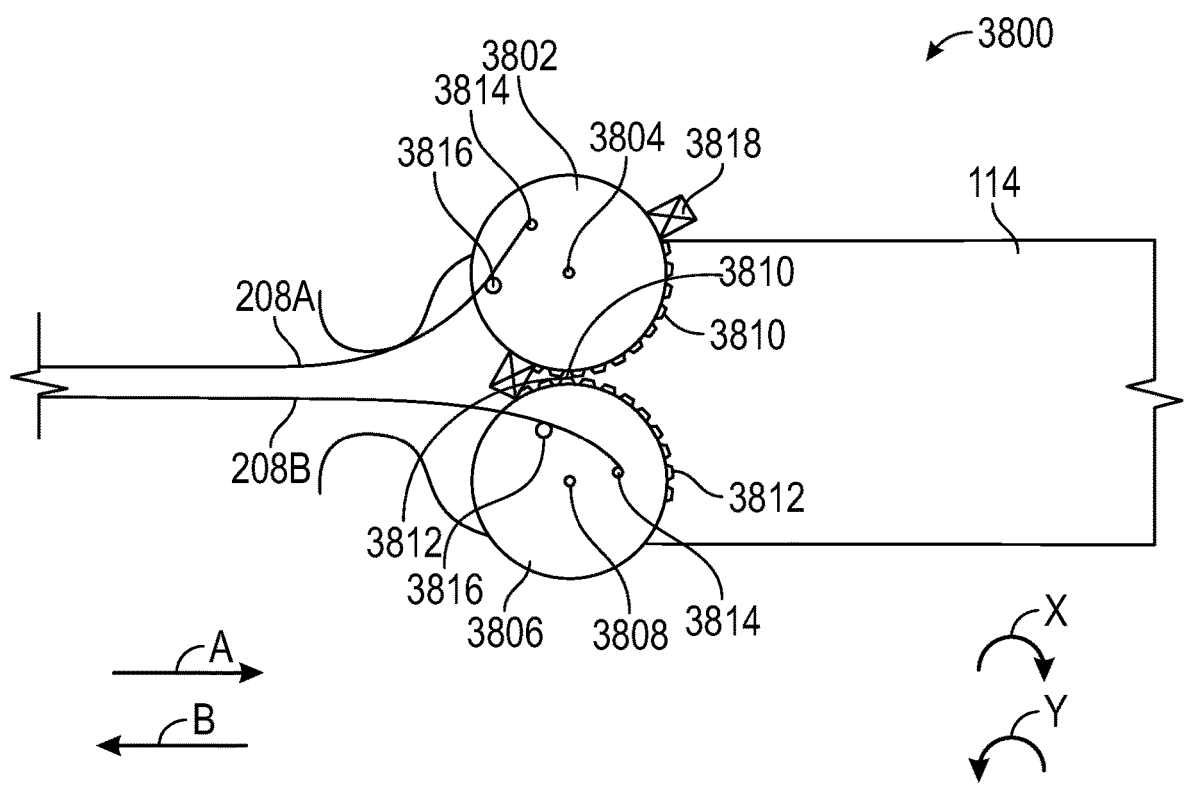
Figure 38B:
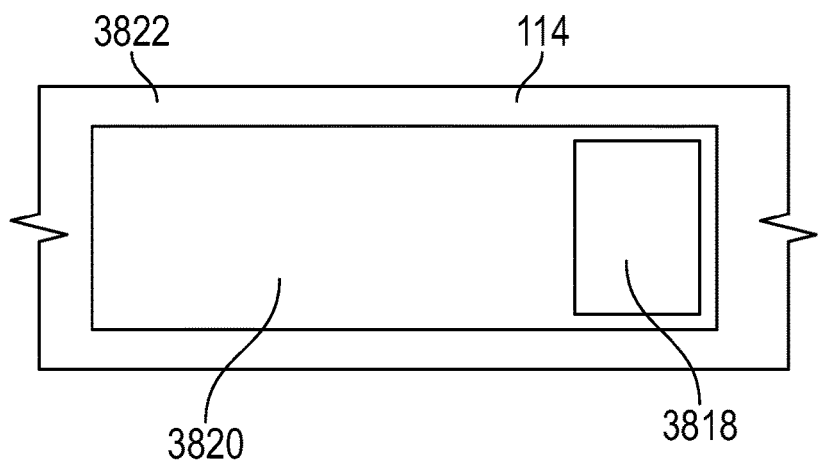

In addition to the embodiment shown with reference to FIGS. 37A and 37B, articulation of the cutting implement 108 can be controlled via an articulation control assembly 3800 disposed within the handheld surgical instrument housing 114, as shown with respect to FIGS. 38A and 38B. In an embodiment, the articulation control assembly 3800 can include a first biasing mechanism 3802 disposed about a pivot 3804 along with a second biasing mechanism 3806 disposed about a pivot 3808. The first biasing mechanism 3802 can include gear teeth 3810 and the second biasing mechanism 3810 can include gear teeth 3812, where the first biasing mechanism gear teeth 3810 can operatively engage with the second biasing mechanism gear teeth 3812.

The first biasing mechanism 3802 and the second biasing mechanism 3806 each include anchor points 3814 and 3816 that are configured to anchor the flat pull wires 208A and 208B with each of the first biasing mechanism 3802 and the second biasing mechanism 3806, respectively. In an embodiment, the flat pull wires 208A and B may anchor with the anchor points 3814 and 3816 with soldering, spot welding, threaded fasteners, rivets, or the like. Thus, when the first biasing mechanism 3802 and the second biasing mechanism 3806 rotate, the flat pull wires 208A and 208B rotate with the first biasing mechanism 3802 and the second biasing mechanism 3806.

In an embodiment, the articulation control assembly 3800 can include an actuator 3818, which can be engaged by a user to rotate the first biasing mechanism along the direction X and the direction Y. In an embodiment, the actuator 3818 can protrude from an opening 3820 at an area 3822 of the handheld surgical instrument housing 114, as shown with regards to FIGS. 38A and 38B. Here, when a user rotates the first biasing mechanism 3802 in the direction X, by virtue of the first biasing mechanism gear teeth 3810 engaging with the second biasing mechanism gear teeth 3812, the second biasing mechanism can rotate in the direction Y. Moreover, as the first biasing mechanism 3802 rotates along direction X, by virtue of the flat pull wire 208A being anchored to the first biasing mechanism 3802 via the anchor points 3814 and 3816, the flat pull wire 208A can move in the direction A. As the second biasing mechanism 3806 rotates along direction Y, by virtue of the flat pull wire 208B being anchored to the second biasing mechanism 3806 via the anchor points 3814 and 3816, the flat pull wire 208B can move in the direction B. Due to the movement of the flat pull wire 208A along the direction A along with movement of the flat pull wire 208B along the direction B, the cutting implement 108 can articulate such that the cutting implement 108 can have positive articulation as described herein.

In addition, when a user rotates the first biasing mechanism 3802 in the direction Y using the actuator 3818, by virtue of the first biasing mechanism gear teeth 3810 engaging with the second biasing mechanism gear teeth 3812, the second biasing mechanism can rotate in the direction X. As the first biasing mechanism 3802 rotates along direction Y, by virtue of the flat pull wire 208A being anchored to the first biasing mechanism 3802 via the anchor points 3814 and 3816, the flat pull wire 208A can move in the direction B. As the second biasing mechanism 3806 rotates along direction X, by virtue of the flat pull wire 208B being anchored to the second biasing mechanism 3806 via the anchor points 3814 and 3816, the flat pull wire 208B can move in the direction A. Due to the movement of the flat pull wire 208A along the direction B along with movement of the flat pull wire 208B along the direction A, the cutting implement 108 can articulate such that the cutting implement 108 can have negative articulation as described herein.

Figure 39:
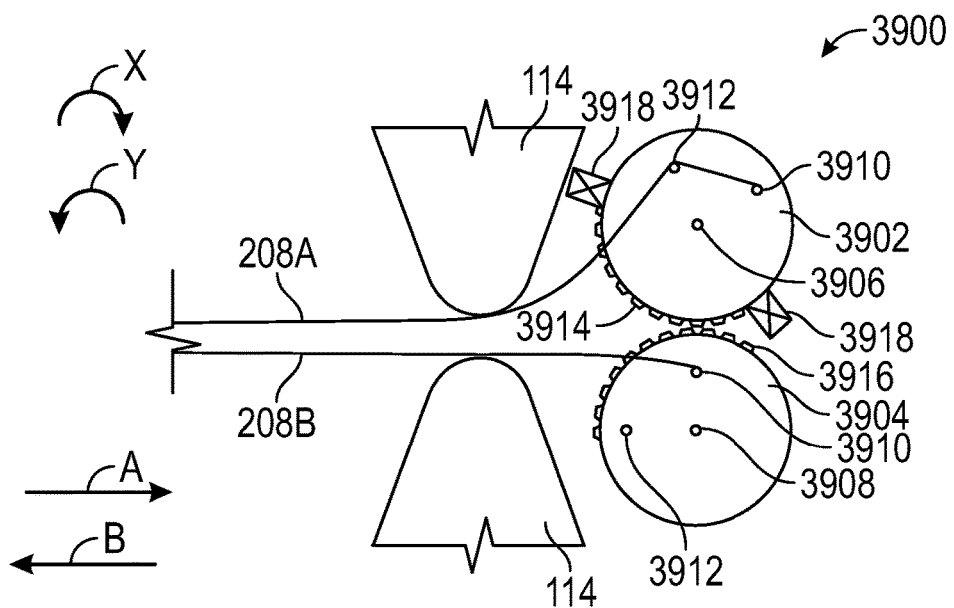

In addition to the embodiment shown with reference to FIGS. 38A and 38B, articulation of the cutting implement 108 can be controlled via an articulation control assembly 3900 disposed within the handheld surgical instrument housing 114, as shown with respect to FIG. 39. In an embodiment, the articulation control assembly 3900 can include a first biasing mechanism 3902 and a second biasing mechanism 3904. The first biasing mechanism 3902 can include a pivot 3906 about which the first biasing mechanism 3902 can rotate along the directions X and Y. The second biasing mechanism 3904 can include a pivot 3908 about which the second biasing mechanism 3904 can rotate along the directions X and Y. Each of the first biasing mechanism 3902 and the second biasing mechanism 3904 can include anchor points 3910 to which the flat pull wires 208A and 208B can anchor to each of the first biasing mechanism 3902 and the second biasing mechanism 3904. In an embodiment, the flat pull wires 208A and 208B can anchor with the anchor points 3910 with soldering, spot welding, threaded fasteners, rivets, or the like. Thus, when the first biasing mechanism 3902 and the second biasing mechanism 3904 rotate, the flat pull wires 208A and 208B rotate with the first biasing mechanism 3902 and the second biasing mechanism 3806, respectively. Moreover, each of the first biasing mechanism 3902 and the second biasing mechanism 3904 can include guides 3912, which can respectively guide the flat pulls wires 208A and 208B during actuation of the first biasing mechanism 3902 and the second biasing mechanism 3904.

In addition, the first biasing mechanism 3902 can include gear teeth 3914 and the second biasing mechanism 3904 can include gear teeth 3916. In an embodiment, the first biasing mechanism gear teeth 3914 can cooperatively engage with the second biasing mechanism gear teeth 3916 such that when a user rotates the first biasing mechanism 3902 via an actuator 3918 along the direction X, the second biasing mechanism 3904 can rotate along the direction Y. As the first biasing mechanism 3902 rotates along the direction X, the flat pull wire 208A can move along the direction A and the flat pull wire 208B moves along the direction B, thereby causing positive articulation of the cutting implement 108, as discussed herein.

In addition, when a user rotates the first biasing mechanism 3902 via the actuator 3918 along the direction Y, the second biasing mechanism 3904 can rotate along the direction X. As the first biasing mechanism 3902 rotates along the direction Y, the flat pull wire 208A can move along the direction B and the flat pull wire 208B moves along the direction A, thereby causing negative articulation of the cutting implement 108, as discussed herein. It should be noted that the embodiments discussed with reference to FIGS. 8-10 may be implemented with the embodiments discussed with reference to FIGS. 38 and 39.

Figure 40:
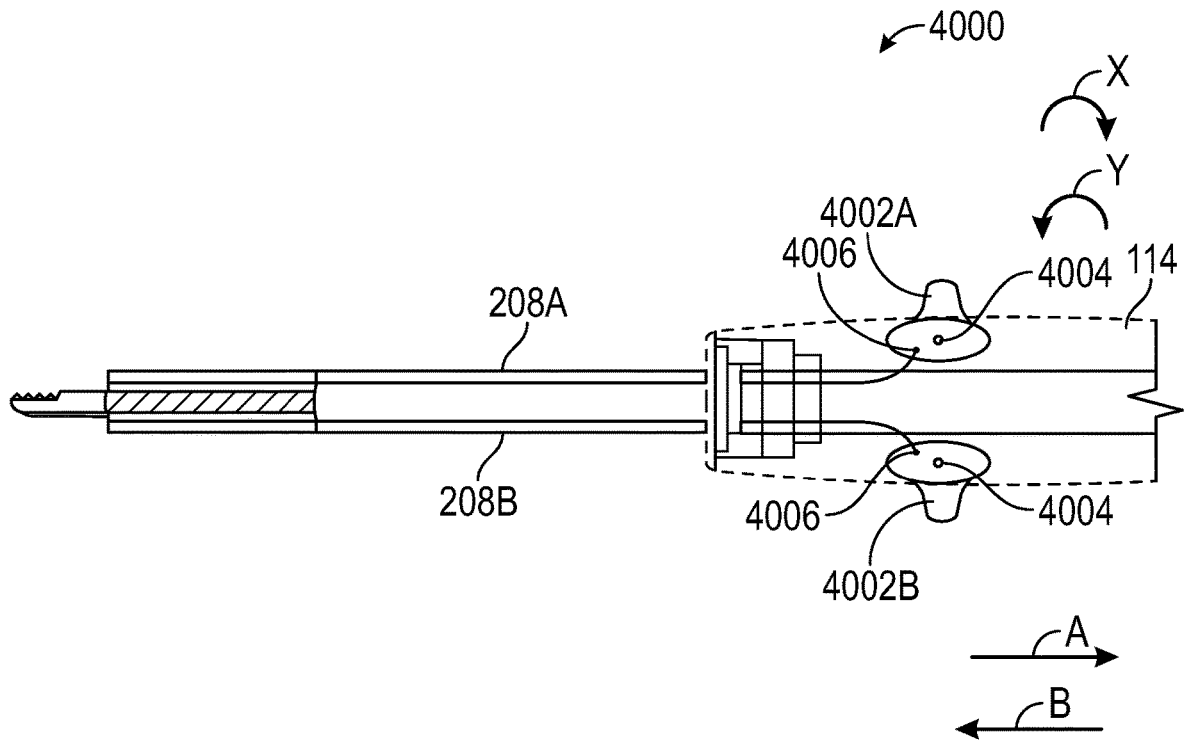

Besides the embodiment shown with reference to FIG. 39, articulation of the cutting implement 108 can be controlled via an articulation control assembly 4000 disposed within the handheld surgical instrument housing 114, as shown with respect to FIG. 40. In an embodiment, the articulation control assembly 4000 can include rocker switches 4002A and 4002B having a pivot 4004 about which the rocker switches 4002A and 4002B pivot. The rocker switches 4002A and 4002B can also include anchor points 4006 to which flat pull wires 208A and 208B anchor. The flat pull wires 208A and 208B can anchor to the anchor points 4006 with soldering, spot welding, threaded fasteners, rivets, or the like. A user can articulate the cutting implement 108 using the rocker switches 4002A and 4002B. For example, a user can rotate the rocker switch 4002A along the direction Y while rotating the rocker switch 4002B along the direction Y. As the user rotates the rocker switch 4002A along the direction Y, the flat pull wire 208A can move along the direction A. In addition, as the user rotates the rocker switch 4002B along the direction Y, the flat pull wire 208B can move along the direction B. As the flat pull wire 208A moves along the direction A and the flat pull wire 208A moves along the direction B, the cutting implement 108 can articulate such that the cutting implement 108 can have positive articulation as described herein.

As another example, a user can rotate the rocker switch 4002A along the direction X while rotating the rocker switch 4002B along the direction X. As the user rotates the rocker switch 4002A along the direction X, the flat pull wire 208A can move along the direction B. In addition, as the user rotates the rocker switch 4002B along the direction X, the flat pull wire 208B can move along the direction A. As the flat pull wire 208A moves along the direction B and the flat pull wire 208A moves along the direction A, the cutting implement 108 can articulate such that the cutting implement 108 can have negative articulation as described herein.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:

1. A handheld surgical instrument, comprising:
a handpiece;
a shaft extending from a proximal end of the handpiece;
a cutting implement disposed at a distal end of the shaft;
an articulation portion disposed proximate to the cutting implement, the articulation portion including:
a set of first slits; and
a set of second slits opposite the set of first slits;
a first flat pull wire disposed in the articulation portion;
a second flat pull wire disposed in the articulation portion; and
an articulation control assembly disposed at the handpiece, the articulation control assembly comprising:
an articulator that includes a first anchor point coupled with the first flat pull wire and a second anchor point coupled with the second flat pull wire, wherein the articulator moves the first flat pull wire in a first direction and moves the second flat pull wire in a second direction opposite the first direction when the articulator rotates;
a first spline;
a first actuator coupled with the first spline;
a second spline; and
a second actuator coupled with the second spline, wherein one of the first spline and the second spline engages with the articulator when the other of the first spline and the second spline disengages with the articulator.

2. The handheld surgical instrument of claim 1, wherein the set of first slits are offset from the set of second slits.

3. The handheld surgical instrument of claim 1, wherein the articulation portion includes a tube and the set of first slits are disposed at a first side of the tube and the set of second slits are disposed at a second side of the tube.

4. The handheld surgical instrument of claim 1, wherein the articulator is a gear.

5. The handheld surgical instrument of claim 1, wherein the articulator moves the first flat pull wire in the first direction and moves the second flat pull wire in the second direction opposite the first direction when the first spline engages with the articulator.

6. The handheld surgical instrument of claim 5, wherein the articulator moves the first flat pull wire in the second direction and moves the second flat pull wire in the first direction opposite the second direction when the second spline engages with the articulator.

7. A handheld surgical instrument, comprising:
a handpiece;
a shaft extending from a proximal end of the handpiece;
a cutting implement disposed at a distal end of the shaft;
an articulation portion disposed proximate to the cutting implement, wherein the articulation portion includes compressible springs;
a first flat pull wire disposed within the articulation portion;
a second flat pull wire disposed within the articulation portion opposite the first flat pull wire; and
an articulation control assembly disposed at the handpiece, the articulation control assembly comprising:
an articulator that includes a first anchor point coupled with the first flat pull wire and a second anchor point coupled with the second flat pull wire, wherein the articulator moves the first flat pull wire in a first direction and moves the second flat pull wire in a second direction opposite the first direction when the articulator rotates;
a first spline;
a first actuator coupled with the first spline;
a second spline; and
a second actuator coupled with the second spline, wherein one of the first spline and the second spline engages with the articulator when the other of the first spline and the second spline disengages with the articulator.

8. The handheld surgical instrument of claim 7, wherein the articulator is a gear.

9. The handheld surgical instrument of claim 7, wherein the articulator moves the first flat pull wire in the first direction and moves the second flat pull wire in the second direction opposite the first direction when the first spline engages with the articulator.

10. The handheld surgical instrument of claim 9, wherein the articulator moves the first flat pull wire in the second direction and moves the second flat pull wire in the first direction opposite the second direction when the second spline engages with the articulator.

11. A handheld surgical instrument, comprising:
a handpiece;

a shaft extending from a proximal end of the handpiece;
a cutting implement disposed at a distal end of the shaft;
an articulation portion disposed proximate to the cutting implement, the articulation portion including:
a set of first slits;
a set of second slits opposite the set of first slits;
a first passageway disposed in each slit of the set of first slits; and
a second passageway disposed in each slit of the set of second slits;
a first flat pull wire disposed in the first passageway and anchored adjacent to the cutting implement;
a second flat pull wire disposed in the second passageway and anchored adjacent to the cutting implement; and
an articulation control assembly disposed at the handpiece, the articulation control assembly comprising:
an articulator that includes a first anchor point coupled with the first flat pull wire and a second anchor point coupled with the second flat pull wire, wherein the articulator moves the first flat pull wire in a first direction such that the first flat pull wire causes articulation of the cutting implement at the articulation portion and moves the second flat pull wire in a second direction opposite the first direction when the articulator rotates;
a first spline;
a first actuator coupled with the first spline;
a second spline; and
a second actuator coupled with the second spline, wherein one of the first spline and the second spline engages with the articulator when the other of the first spline and the second spline disengages with the articulator.

* * * * *